(12) United States Patent
Ji et al.

(10) Patent No.: US 8,853,241 B2
(45) Date of Patent: *Oct. 7, 2014

(54) BIARYL SUBSTITUTED AZABICYCLIC ALKANE DERIVATIVES

(75) Inventors: Jianguo Ji, Libertyville, IL (US); Tao Li, Grayslake, IL (US); Kevin B. Sippy, Antioch, IL (US); Chih-Hung Lee, Vernon Hills, IL (US); Murali Gopalakrishnan, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 852 days.

This patent is subject to a terminal disclaimer.

(21) Appl. No.: 13/014,947

(22) Filed: Jan. 27, 2011

(65) Prior Publication Data

US 2011/0124676 A1 May 26, 2011

Related U.S. Application Data

(62) Division of application No. 12/274,529, filed on Nov. 20, 2008, now Pat. No. 7,902,222.

(60) Provisional application No. 60/989,538, filed on Nov. 21, 2007.

(51) Int. Cl.
*A61K 31/46* (2006.01)
*C07D 451/06* (2006.01)
*C07D 451/04* (2006.01)

(52) U.S. Cl.
CPC .............. *C07D 451/04* (2013.01); *A61K 31/46* (2013.01); *C07D 451/06* (2013.01)
USPC ............................ 514/304; 546/125; 546/126

(58) Field of Classification Search
CPC ................................ A61K 31/46; C07D 451/06
USPC .................................... 514/304; 546/125, 126
See application file for complete search history.

(56) References Cited

U.S. PATENT DOCUMENTS

| 7,872,017 | B2 | 1/2011 | Ji et al. | |
| 7,902,222 | B2 * | 3/2011 | Ji et al. | 514/304 |
| 2005/0043347 | A1 | 2/2005 | Betschmann et al. | |
| 2008/0234308 | A2 | 9/2008 | Schrimpf et al. | |

FOREIGN PATENT DOCUMENTS

| WO | WO0071520 A2 | 11/2000 |
| WO | WO03062235 A1 | 7/2003 |
| WO | WO2004037823 A1 | 5/2004 |
| WO | WO2006101745 A2 | 9/2006 |

OTHER PUBLICATIONS

Picciotto et al. (Frontiers in Bioscience 2008, 13, 492-504.*
Basmadjian, et al., "Design of Novel Nicotinic Acetylcholine Receptor Agonists with Potential Antinociceptive Activity" in: Pain Mechanisms and Management, Ayrapetian S.N., et al., Eds., IOS Press, 1998. pp. 285-300.
European Search Report for Application No. 10173074; completed Mar. 25, 2011; 3 pages.
Adler L.E., et al., "Schizophrenia, Sensory Gating, and Nicotinic Receptors," Schizophrenia Bulletin, 1998, vol. 24 (2), pp. 189-202.
Cordero-Erausquin M., et al., "Tonic Nicotinic Modulation of Serotoninergic Transmission in the Spinal Cord," Proceedings of the National Academy of Sciences , 2001, vol. 98 (5), pp. 2803-2807.
Cross L.C., et al., "IUPAC Commission on Nomenclature of Organic Chemistry: Rules for the Nomenclature of Organic Chemistry, Section E: Stereochemistry ," Pure and Applied Chemistry, 1976, vol. 45, pp. 11-30.
Friedman J.I., et al., "A Double Blind Placebo Controlled Trial of Donepezil Adjunctive Treatment to Risperidone for the Cognitive Impairment of Schizophrenia," Biological Psychiatry , 2002, vol. 51, pp. 349-357.
Furniss B.S., et al., Vogel's Textbook of Practical Organic Chemistry, 5th Edition, Longman Scientific & Technical, 1989, Table of Contents.
Greene T.W., et al., "Protection for the Amino group," Protective Groups in Organic Synthesis, 1999, Third Edition, pp. 494-653.
Heeschen C., et al., "A Novel Angiogenic Pathway Mediated by Non-Neuronal Nicotinic Acetycholine Receptors," Journal of Clinical Investigation, 2002, vol. 110 (4), pp. 527-536.
Heeschen C., et al., "Nicotine Stimulates Angiogenesis and Promotes Tumor Growth and Atherosclerosis," Nature Medicine, 2001, vol. 7 (7), pp. 833-839.
Higuchi T., et al., "Pro-Drugs as Novel Drug Delivery Systems," American Chemical Society, 1975, Table of Contents.
International Search Report for Application No. PCT/US2008/084148, mailed on Feb. 12, 2009, 3 pages.
Jonnala R.R., et al., "Relationship between the Increased Cell Surface α7 nicotinic Receptor Expression and Neuroprotection Induced by Several Nicotinic Receptor Agonists," Journal of Neuroscience Research, 2001, vol. 66 (4), pp. 565-572.
Kihara T., et al., "Alpha.7 Nicotinic Receptor Transduces Signals to Phosphatidylinositol 3- kinase to Block A .beta.-amyloid-induced Neurotoxicity," Journal of Biological Chemistry, 2001, vol. 276 (17), pp. 13541-13546.
Leonard S., et al., "Smoking and Schizophrenia: Abnormal Nicotinic Receptor Expression," European Journal of Pharmacology, 2000, vol. 393 (1-3), pp. 237-242.
Levin E.D., "Nicotinic Receptor Subtypes and Cognitive Function," Journal of Neurobiology , 2002, vol. 53 (4), pp. 633-640.
Liu Q.S., et al., "Alpha-Amyloid Peptide Blocks the Response of Alpha.7-Containing Nicotinic Receptors on Hippocampal Neurons," Proceedings of the National Academy of Sciences, 2001, vol. 98 (8), pp. 4734-4739.
Pabreza L.A., et al., "[.sup.3H]Cytisine Binding to Nicotinic Cholinergic Receptors in Brain," Molecular Pharmacology, 1990, vol. 39, pp. 9-12.
Paterson D., et al., "Neuronal Nicotinic Receptors in the Human Brain," Progress in Neurobiology, 2000, vol. 61 (1), pp. 75-111.
Poste G., et al., "Lipid Vesicles as Carriers for Introducing Biologically Active Materials into Cells," Methods in Cell Biology, 1976, vol. 14, pp. 33-71.
Rautio J., et al, "Prodrugs: Design and Clinical Applications," Nature Reviews Drug Discovery, 2008, vol. 7 (3), pp. 255-270.

(Continued)

*Primary Examiner* — Joseph Kosack
*Assistant Examiner* — Matthew Coughlin
(74) *Attorney, Agent, or Firm* — Lisa V. Mueller; Michael Best & Friedrich LLP

(57) ABSTRACT

The invention relates to biaryl substituted azabicyclic alkane derivatives, compositions comprising such compounds, and methods of treating conditions and disorders using such compounds and compositions.

17 Claims, No Drawings

(56) References Cited

OTHER PUBLICATIONS

Rollema H., et al., "Rationale, Pharmacology and Clinical efficacy of Partial agonists of alpha4beta2 nACh Receptors for Smoking Cessation," Trends Pharmacological Sciences, 2007, vol. 28 (7), pp. 316-325.

Rose J., et al., "Multiple Brain Pathways and Receptors Underlying tobacco Addiction," Biochemical Pharmacology, 2007, vol. 74 (8), pp. 1263-1270.

Rowley M., et al., "Current and Novel Approaches to the Drug Treatment of Schizophrenia," Journal of Medicinal Chemistry, 2001, vol. 44 (4), pp. 477-501.

Shimohama S., et al., "Nicotinic Alpha 7 Receptors Protect Against Glutamate Neurotoxicity and Neuronal Ischemic Damage," Brain Research, 1998, vol. 779 (1-2), pp. 359-363.

Smith D.A., "Do Prodrugs Deliver?," Current Opinion in Drug Discovery and Development, 2007, vol. 10 (5), 550-559.

Solinas M., et al., "Nicotinic 7 Receptors as a New Target for Treatment of Cannabis Abuse," The Journal of Neuroscience, 2007, vol. 27 (21), pp. 5615-5620.

Son J.H., et al., "Evidence Suggesting that the Mouse Sperm Acrosome Reaction Initiated by the Zona Pellucida Involves An Alpha.7 Nicotinic Acetylcholine Receptor," Biology of Reproduction, 2003, vol. 68 (4), pp. 1348-1351.

Steensland P., et al., "Varenicline, an 4[1]2 Nicotinic Acetylcholine Receptor Partial Agonist, Selectively Decreases Ethanol Consumption and Seeking ," Proceedings of the National Academy of Sciences, 2007, vol. 104 (30), pp. 12518-12523.

Stevens K.E., et al., "Selective A7-Nicotinic Agonists Normalize Inhibition of Auditory Response in Dba Mice," Psychopharmacology, 1998, vol. 136 (4), pp. 320-327.

Testa B., "Prodrugs: Bridging Pharmacodynamic/Pharmacokinetic Gaps," Current Opinion in Chemical Biology, 2009, vol. 13 (3), pp. 338-344.

Wang B., et al., Drug Delivery: Principles and Applications, John Wiley & Sons, Inc., 2005, pp. 136-137.

Wang H., et al., "Nicotinic Acetylcholine Receptor Alpha7 Subunit is an Essential Regulator of Inflammation," Nature, 2003, vol. 421 (6921), pp. 384-388.

Wolter M., et al., "Copper-Catalyzed Coupling of Aryl Iodides with Aliphatic Alcohols," Organic Letters, 2002, vol. 4 (6), pp. 973-976.

\* cited by examiner

US 8,853,241 B2

BIARYL SUBSTITUTED AZABICYCLIC ALKANE DERIVATIVES

CROSS-REFERENCE TO RELATED APPLICATION

This application is a division of U.S. patent application Ser. No. 12/274,529, filed on Nov. 20, 2008, which claims priority from U.S. Patent Application No. 60/989,538, filed on Nov. 21, 2007, each of which is herein incorporated by reference in its entirety.

FIELD OF THE INVENTION

The invention relates to biaryl substituted azabicyclic alkane derivatives, more particularly 5-membered heteroaryl ring substituted azabicyclic alkane derivatives, compositions comprising such compounds, and methods of treating conditions and disorders using such compounds and compositions.

DESCRIPTION OF RELATED TECHNOLOGY

Nicotinic acetylcholine receptors (nAChRs) are widely distributed throughout the central (CNS) and peripheral (PNS) nervous systems. Such receptors play an important role in regulating CNS function, particularly by modulating release of a wide range of neurotransmitters, such as acetylcholine, norepinephrine, dopamine, serotonin and GABA. Consequently, nicotinic receptors mediate a very wide range of physiological effects, and have been targeted for therapeutic treatment of disorders relating to cognitive function, learning and memory, neurodegeneration, pain and inflammation, psychosis and sensory gating, mood and emotion, among others.

The plant alkaloid nicotine interacts with all subtypes of the nAChRs. While nicotine has been demonstrated to have many biological activities, not all of the effects mediated by nicotine are desirable. For example, nicotine exerts gastrointestinal and cardiovascular side effects at therapeutic doses, and it is addictive and acutelyoxic. Ligands that are selective for interacting with only certain subtypes of the nAChR offer potential for achieving beneficial therapeutic effects with an improved margin of safety.

Many subtypes of the nAChR have been observed in the CNS and periphery. Each subtype has a different effect on regulating overall physiological function. Typically, nAChRs are ion channels that are constructed from pentamers. At least 12 subunit proteins, $\alpha 2$-$\alpha 10$ and $\beta 2$-$\beta 4$, have been identified in neuronal tissue. These subunits provide for a great variety of homomeric and heteromeric combinations that account for the diverse receptor subtypes. For example, the predominant receptor that is responsible for high affinity binding of nicotine in brain tissue has composition $(\alpha 4)_2(\beta 2)_3$ (the $\alpha 4\beta 2$ subtype), while another major population of receptors is homopentamers $(\alpha 7)_5$ (the $\alpha 7$ subtype).

The a7 and a4β2 nAChRs: Receptors with Many Roles

The $\alpha 7$ and $\alpha 4\beta 2$ nAChRs play roles in multifarious processes, including cognitive function, protection against neuron degeneration, pain relief and schizophrenia; as well as other functions that appear less related to neuronal activity, such as angiogenesis and the sperm acrosome reaction during egg fertilization.

The $\alpha 7$ and $\alpha 4\beta 2$ nAChRs have been shown to play a significant role in enhancing cognitive function, including aspects of learning, memory and attention (Levin, E. D., *J. Neurobiol.* 53: 633-640, 2002). For example, $\alpha 7$ nAChRs have been linked to conditions and disorders related to attention deficit disorder (ADD), attention deficit hyperactivity disorder (ADHD), Alzheimer's disease (AD), mild cognitive impairment, senile dementia, dementia associated with Lewy bodies, dementia associated with Down's syndrome, AIDS dementia, Pick's Disease, as well as cognitive deficits associated with schizophrenia, among other systemic activities. The $\alpha 4\beta 2$ receptor subtype is implicated in attention, cognition, schizophrenia, epilepsy, and pain control (Paterson and Norberg, *Progress in Neurobiology* 61 75-111, 2000).

In addition to their roles in enhancing cognitive function, $\alpha 7$-containing nAChRs have been shown to be involved in the neuroprotective effects of nicotine both in vitro (Jonnala, R. B. and Buccafusco, J. J., *J. Neurosci. Res.* 66: 565-572, 2001) and in vivo (Shimohama, S. et al., *Brain Res.* 779: 359-363, 1998). More particularly, neurodegeneration underlies several progressive CNS disorders, such as Alzheimer's disease, Parkinson's disease, amyotrophic lateral sclerosis, Huntington's disease, dementia with Lewy bodies, as well as diminished CNS function resulting from traumatic brain injury. For example, the impaired function of $\alpha 7$ nAChRs by $\beta$-amyloid peptides linked to Alzheimer's disease has been implicated as a key factor in development of the cognitive deficits associated with the disease (Liu, Q.-S., Kawai, H., Berg, D. K., *PNAS* 98: 4734-4739, 2001). The activation of $\alpha 7$ nAChRs has been shown to block this neurotoxicity (Kihara, T. et al., *J. Biol. Chem.* 276: 13541-13546, 2001). As such, selective ligands that enhance $\alpha 7$ activity can counter the deficits of Alzheimer's and other neurodegenerative diseases.

Schizophrenia is a complex disease that is characterized by abnormalities in perception, cognition, and emotions. Significant evidence implicates the involvement of $\alpha 7$ nAChRs in this disease, including a measured deficit of these receptors in post-mortem patients (Leonard, S. *Eur. J. Pharmacol.* 393: 237-242, 2000). Deficits in sensory processing (gating) are one of the hallmarks of schizophrenia. These deficits can be normalized by nicotinic ligands that operate at the $\alpha 7$ nAChR (Adler L. E. et al., *Schizophrenia Bull.* 24: 189-202, 1998; Stevens, K. E. et al., *Psychopharmacology* 136: 320-327, 1998).

Cognitive impairment associated with schizophrenia often limits the ability of patients to function normally, a symptom not adequately treated by commonly available treatments, for example, treatment with an atypical antipsychotic. (Rowley, M. et al, *J. Med. Chem.* 44: 477-501, 2001). Such cognitive deficit has been linked to dysfunction of the nicotinic cholinergic system, in particular with decreased activity receptors. (Friedman, J. I. et al, *Biol Psychiatry,* 51: 349-357, 2002).

Angiogenesis, a process involved in the growth of new blood vessels, is important in beneficial systemic functions, such as wound healing, vascularization of skin grafts, and enhancement of circulation, for example, increased circulation around a vascular occlusion. Non-selective nAChR agonists like nicotine have been shown to stimulate angiogenesis (Heeschen, C. et al, *Nature Medicine* 7: 833-839, 2001). Improved angiogenesis has been shown to involve activation of the $\alpha 7$ nAChR (Heeschen, C. et al., *J. Clin. Invest.* 110: 527-536, 2002).

A population of $\alpha 7$ nAChRs in the spinal cord modulate serotonergic transmission that have been associated with the pain-relieving effects of nicotinic compounds (Cordero-Erausquin, M. and Changeux, J.-P. *PNAS* 98:2803-2807, 2001). The $\alpha 7$ nAChR ligands demonstrate therapeutic potential for the treatment of pain states, including acute pain, post-surgical pain, as well as chronic pain states including inflammatory pain and neuropathic pain. Moreover, $\alpha 7$ nAChRs are expressed on the surface of primary macrophages that are involved in the inflammation response. Activation of the $\alpha 7$ receptor inhibits release of TNF and other cytokines that trigger the inflammation response (Wang, H. et al, *Nature* 421: 384-388, 2003). TNF-mediated diseases include, for example, rheumatoid arthritis, Crohn's disease, ulcerative colitis, inflammatory bowel disease, organ transplant rejection, acute immune disease associated with organ transplantation, chronic immune disease associated with organ transplantation, septic shock, toxic shock syndrome, sepsis syndrome, depression, and rheumatoid spondylitis.

The mammalian sperm acrosome reaction is an exocytosis process important in fertilization of the ovum by sperm. Activation of an α7 nAChR on the sperm cell has been shown to be essential for the acrosome reaction (Son, J.-H. and Meizel, S. *Biol. Reproduct.* 68: 1348-1353 2003).

The activity at both α7 and α4β2 nAChRs can be modified or regulated by the administration of subtype-selective nAChR ligands. The ligands can exhibit antagonist, agonist, or partial agonist properties. Compounds that function as positive allosteric modulators are also known.

Although compounds, such as nicotine, that nonselectively modulate nicotinic receptor subtypes including the α4β2 and α7 nAChRs are known, compounds that interact selectively with the α7-containing neuronal nAChRs, α4β2 nAChRs, or both α7 and α4β2 nAChRs are desirable because of these receptors' many roles in pain, cognition, disorders and diseases.

SUMMARY OF THE INVENTION

The invention is directed to biaryl substituted azabicyclic compounds as well as compositions comprising such compounds, and method of using the same.

One aspect of the present invention is directed toward a compound of formula (I)

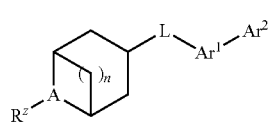

(I)

or a pharmaceutically acceptable salt, ester, amide, or prodrug thereof, wherein n is 1, 2 or 3;

A is —N— or —N⁺—O⁻—;

$R^z$ is hydrogen, alkyl, cycloalkyl and arylalkyl;

L is selected from the group consisting of O, S, and —N($R^a$)—; wherein $R^a$ is selected from the group consisting of hydrogen, alkyl and alkylcarbonyl;

$Ar^1$ is a 5-membered heteroaryl group;

$Ar^2$ is an aryl or heteroaryl group.

Another aspect of the invention relates to pharmaceutical compositions comprising compounds of the invention. Such compositions can be administered in accordance with a method of the invention, typically as part of a therapeutic regimen for treatment or prevention of conditions and disorders related to nAChR activity, and more particularly α7 nAChR activity, α4β2 nAChR activity, or both α7 nAChR activity and α4β2 nAChR activity.

Yet another aspect of the invention relates to a method of modulating both α7 and α4β2 nAChR activity. The method is useful for treating, preventing or both treating and preventing conditions and disorders related to both α7 and α4β2 nAChR activity, particularly in mammals.

A further aspect of the invention relates to a method of selectively modulating nAChR activity, for example α7 nAChR activity. The method is useful for treating, preventing or both treating and preventing conditions and disorders related to α7 nAChR activity in mammals. More particularly, the method is useful for conditions and disorders related to attention deficit disorder, attention deficit hyperactivity disorder (ADHD), Alzheimer's disease (AD), schizophrenia, mild cognitive impairment, age-associated memory impairment (AAMI), senile dementia, AIDS dementia, Pick's Disease, dementia associated with Lewy bodies, dementia associated with Down's syndrome, schizophrenia, amyotrophic lateral sclerosis, Huntington's disease, diminished CNS function associated with traumatic brain injury, acute pain, post-surgical pain, chronic pain, inflammatory pain, neuropathic pain, infertility, lack of circulation, need for new blood vessel growth associated with wound healing, more particularly circulation around a vascular occlusion, need for new blood vessel growth associated with vascularization of skin grafts, ischemia, inflammation, sepsis, wound healing, and other complications associated with diabetes, among other systemic and neuroimmunomodulatory activities.

A method of selectively modulating nAChR activity, for example α4β2 nAChR activity, also is contemplated.

The compounds, compositions comprising the compounds, methods for using the compounds, and processes for preparing the compounds, as well as intermediates obtained in such processes, are further described herein.

DETAILED DESCRIPTION

First, terms are defined. Secondly, the compounds of the invention are described and shown how to be made, including many examples of their syntheses. Finally the use of these compounds is then discussed and exemplified.

DEFINITIONS OF TERMS

As used throughout this specification and the appended claims, the following terms have the following meanings:

The term "alkenyl" means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond. Representative examples of alkenylene include, but are not limited to, —CH=CH—, —CH=CH₂CH₂—, and —CH=C(CH₃)CH₂—.

The term "alkenyloxy" means an alkenyl group, as defined herein, appended to the parent molecular moiety through an oxygen atom. Representative examples of alkenyloxy include, but are not limited to, allyloxy, 2-butenyloxy and 3-butenyloxy.

The term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl" means an alkoxyalkoxy group, as defined herein, appended to the parent molecular moiety through an alkyl group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl" means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkoxysulfonyl" means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 10 carbon atoms. Representative examples of alkylene include, but are not limited to, $-CH_2-$, $-CH(CH_3)-$, $-C(CH_3)_2-$, $-CH_2CH_2-$, $-CH_2CH_2CH_2-$, $-CH_2CH_2CH_2CH_2-$, and $-CH_2CH(CH_3)CH_2-$.

The term "alkylsulfinyl" means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl" means an alkylsulfinyl group, as defined herein, appended to the parent molecular moiety through an alkyl group, as defined herein. Representative examples of alkylsulfinylalkyl include, but are not limited to, methylsulfinylmethyl and ethylsulfinylmethyl.

The term "alkylsulfonyl" means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl" means an alkylsulfonyl group, as defined herein, appended to the parent molecular moiety through an alkyl group, as defined herein. Representative examples of alkylsulfonylalkyl include, but are not limited to, methylsulfonylmethyl and ethylsulfonylmethyl.

The term "alkylthio" means an alkyl group, as defined herein, appended to the parent molecular moiety through a sulfur atom. Representative examples of alkylthio include, but are not limited, methylthio, ethylthio, tert-butylthio, and hexylthio.

The term "alkylthioalkyl" means an alkylthio group, as defined herein, appended to the parent molecular moiety through an alkyl group, as defined herein. Representative examples of alkylthioalkyl include, but are not limited, methylthiomethyl and 2-(ethylthio)ethyl.

The term "alkynyl" means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkynylene" means a divalent group derived from a straight or branched chain hydrocarbon of from 2 to 10 carbon atoms containing at least one triple bond. Representative examples of alkynylene include, but are not limited to, $-C\equiv C-$, $-CH_2C\equiv C-$, $-CH(CH_3)CH_2C\equiv C-$, $-C\equiv CCH_2-$, and $-C\equiv CCH(CH_3)CH_2-$.

The term "alkynyloxy" means an alkynyl group, as defined herein, appended to the parent molecular moiety through an oxygen atom. Representative examples of alkynyloxy include, but are not limited to, 2-propynyloxy and 2-butynyloxy.

The term "aryl," means phenyl, a bicyclic aryl or a tricyclic aryl. The bicyclic aryl is naphthyl, a phenyl fused to a cycloalkyl, or a phenyl fused to a cycloalkenyl. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, or a bicyclic aryl fused to a cycloalkyl, or a bicyclic aryl fused to a cycloalkenyl, or a bicyclic aryl fused to a phenyl. Representative examples of tricyclic aryl ring include, but are not limited to, azulenyl, dihydroanthracenyl, fluorenyl, and tetrahydrophenanthrenyl.

The aryl groups of this invention can be substituted with 1, 2, 3, 4 or 5 substituents independently selected from alkenyl, alkoxy, alkoxyalkoxy, alkoxyalkoxyalkyl, alkoxyalkyl, alkoxycarbonyl, alkoxycarbonylalkyl, alkyl, alkylcarbonyl, alkylcarbonylalkyl, alkylcarbonyloxy, alkylsulfinyl, alkylsulfinylalkyl, alkylsulfonyl, alkylsulfonylalkyl, alkylthio, alkylthioalkyl, alkynyl, carboxy, carboxyalkyl, cyano, cyanoalkyl, formyl, formylalkyl, halogen, haloalkyl, hydroxy, hydroxyalkyl, mercapto, nitro, $-NZ_1Z_2$, and $(NZ_3Z_4)$carbonyl.

The term "arylalkoxy" means an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkoxycarbonyl" means an arylalkoxy group, as defined herein, appended to the parent molecular moiety through a carbonyl group, as defined herein. Representative examples of arylalkoxycarbonyl include, but are not limited to, benzyloxycarbonyl and naphth-2-ylmethoxycarbonyl.

The term "arylalkyl" means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylalkylthio" means an arylalkyl group, as defined herein, appended to the parent molecular moiety through a sulfur atom. Representative examples of arylalkylthio include, but are not limited to, 2-phenylethylthio, 3-naphth-2-ylpropylthio, and 5-phenylpentylthio.

The term "arylcarbonyl" means an aryl group, as defined herein, appended to the parent molecular moiety through a carbonyl group, as defined herein. Representative examples of arylcarbonyl include, but are not limited to, benzoyl and naphthoyl.

The term "aryloxy" means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "aryloxyalkyl" means an aryloxy group, as defined herein, appended to the parent molecular moiety through an alkyl group, as defined herein. Representative examples of aryloxyalkyl include, but are not limited to, 2-phenoxyethyl, 3-naphth-2-yloxypropyl and 3-bromophenoxymethyl.

The term "arylthio" means an aryl group, as defined herein, appended to the parent molecular moiety through a sulfur atom. Representative examples of arylthio include, but are not limited to, phenylthio and 2-naphthylthio.

The term "arylthioalkyl" means an arylthio group, as defined herein, appended to the parent molecular moiety through an alkyl group, as defined herein. Representative examples of arylthioalkyl include, but are not limited to, phenylthiomethyl, 2-naphth-2-ylthioethyl, and 5-phenylthiomethyl.

The term "azido" means a —$N_3$ group.

The term "carbonyl" means a —C(=O)— group.

The term "carboxy" means a —$CO_2H$ group.

The term "carboxyalkyl" means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano" means a —CN group.

The term "cyanoalkyl" means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkenyl" means a cyclic hydrocarbon containing from 3 to 8 carbons and containing at least one carbon-carbon double bond formed by the removal of two hydrogens. Representative examples of cycloalkenyl include, but are not limited to, 2-cyclohexen-1-yl, 3-cyclohexen-1-yl, 2,4-cyclohexadien-1-yl and 3-cyclopenten-1-yl.

The term "cycloalkyl" means a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two adjacent or non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane.

The cycloalkyl groups of the invention are optionally substituted with 1, 2, 3, 4 or 5 substituents selected from the group consisting of alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkylthioalkyl, alkynyl, carboxy, cyano, formyl, haloalkoxy, haloalkyl, halogen, hydroxy, hydroxyalkyl, mercapto, oxo, —$NZ_1Z_2$, and ($NZ_3Z_4$)carbonyl.

The term "cycloalkylalkyl" means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "cycloalkylcarbonyl" means cycloalkyl group, as defined herein, appended to the parent molecular moiety through a carbonyl group, as defined herein. Representative examples of cycloalkylcarbonyl include, but are not limited to, cyclopropylcarbonyl, 2-cyclobutylcarbonyl, and cyclohexylcarbonyl.

The term "cycloalkyloxy" means cycloalkyl group, as defined herein, appended to the parent molecular moiety through an oxygen atom, as defined herein. Representative examples of cycloalkyloxy include, but are not limited to, cyclopropyloxy, cyclobutyloxy, cyclopentyloxy, cyclohexyloxy, cycloheptyloxy, and cyclooctyloxy.

The term "cycloalkylthio" means cycloalkyl group, as defined herein, appended to the parent molecular moiety through a sulfur atom, as defined herein. Representative examples of cycloalkylthio include, but are not limited to, cyclopropylthio, cyclobutylthio, cyclopentylthio, cyclohexylthio, cycloheptylthio, and cyclooctylthio.

The term "ethylenedioxy" means a —$O(CH_2)_2O$— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" means a —C(=O)H group.

The term "formylalkyl" means a formyl group, as defined herein, appended to the parent molecular moiety through an alkyl group, as defined herein. Representative examples of formylalkyl include, but are not limited to, formylmethyl and 2-formylethyl.

The term "halo" or "halogen" means —Cl, —Br, —I or —F.

The term "haloalkoxy" means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," means a monocyclic heteroaryl or a bicyclic heteroaryl. The monocyclic heteroaryl is a 5- or 6-membered ring that contains at least one heteroatom selected from the group consisting of nitrogen, oxygen and sulfur. The 5-membered ring contains two double bonds and the 6-membered ring contains three double bonds. The 5- or 6-membered heteroaryl is connected to the parent molecular moiety through any carbon atom or any substitutable nitrogen atom contained within the heteroaryl, provided that proper valance is maintained. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any substitutable nitrogen atom contained within the bicyclic heteroaryl, provided that proper valance is maintained. Representative examples of bicyclic heteroaryl include, but are not limited to, azaindolyl, benzimidazolyl, benzofuranyl, benzoxadiazolyl, benzoisoxazole, benzoisothiazole, benzooxazole, 1,3-benzothiazolyl, benzothiophenyl, cinnolinyl, furopyridine, indolyl, indazolyl, isobenzofuran, isoindolyl, isoquinolinyl, naphthyridinyl, oxazolopyridine, quinolinyl, quinoxalinyl and thienopyridinyl.

The heteroaryl groups of the invention are optionally substituted with 1, 2, 3 or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, nitro, —$NZ_1Z_2$ and ($NZ_3Z_4$)carbonyl. Heteroaryl groups of the invention that are substituted with a hydroxyl group may be present as tautomers. The heteroaryl groups of the invention encompass all tautomers including non-aromatic tautomers.

The term "heteroarylalkoxy" means a heteroaryl group, as defined herein, appended to the parent molecular moiety through an alkoxy group, as defined herein. Representative examples of heteroarylalkoxy include, but are not limited to, fur-3-ylmethoxy, 1H-imidazol-2-ylmethoxy, 1H-imidazol-4-ylmethoxy, 1-(pyridin-4-yl)ethoxy, pyridin-3-ylmethoxy, 6-chloropyridin-3-ylmethoxy, pyridin-4-ylmethoxy, (6-(trifluoromethyl)pyridin-3-yl)methoxy, (6-(cyano)pyridin-3-yl)methoxy, (2-(cyano)pyridin-4-yl)methoxy, (5-(cyano)pyridin-2-yl)methoxy, (2-(chloro)pyridin-4-yl)methoxy, pyrimidin-5-ylmethoxy, 2-(pyrimidin-2-yl)propoxy, thien-2-ylmethoxy, and thien-3-ylmethoxy.

The term "heteroarylalkyl" means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

The term "heteroarylalkylcarbonyl" means a heteroarylalkyl, as defined herein, appended to the parent molecular moiety through a carbonyl group, as defined herein.

The term "heteroarylalkylthio" means a heteroarylalkyl group, as defined herein, appended to the parent molecular moiety through a sulfur atom. Representative examples of heteroarylalkylthio include, but are not limited to, fur-3-ylmethylthio, 1H-imidazol-2-ylmethylthio, 1H-imidazol-4-ylmethylthio, pyridin-3-ylmethylthio, 6-chloropyridin-3-ylmethylthio, pyridin-4-ylmethylthio, (6-(trifluoromethyl)pyridin-3-yl)methylthio, (6-(cyano)pyridin-3-yl)methylthio, (2-(cyano)pyridin-4-yl)methylthio, (5-(cyano)pyridin-2-yl)methylthio, (2-(chloro)pyridin-4-yl)methylthio, pyrimidin-5-ylmethylthio, 2-(pyrimidin-2-yl)propylthio, thien-2-ylmethylthio, and thien-3-ylmethylthio.

The term "heteroarylcarbonyl" means a heteroaryl group, as defined herein, appended to the parent molecular moiety through a carbonyl group, as defined herein. Representative examples of heteroarylcarbonyl include, but are not limited to, fur-3-ylcarbonyl, 1H-imidazol-2-ylcarbonyl, 1H-imidazol-4-ylcarbonyl, pyridin-3-ylcarbonyl, 6-chloropyridin-3-ylcarbonyl, pyridin-4-ylcarbonyl, (6-(trifluoromethyl)pyridin-3-yl)carbonyl, (6-(cyano)pyridin-3-yl)carbonyl, (2-(cyano)pyridin-4-yl)carbonyl, (5-(cyano)pyridin-2-yl)carbonyl, (2-(chloro)pyridin-4-yl)carbonyl, pyrimidin-5-ylcarbonyl, pyrimidin-2-ylcarbonyl, thien-2-ylcarbonyl, and thien-3-ylcarbonyl.

The term "heteroaryloxy" means a heteroaryl group, as defined herein, appended to the parent molecular moiety through an oxygen atom. Representative examples of heteroaryloxy include, but are not limited to, fur-3-yloxy, 1H-imidazol-2-yloxy, 1H-imidazol-4-yloxy, pyridin-3-yloxy, 6-chloropyridin-3-yloxy, pyridin-4-yloxy, (6-(trifluoromethyl)pyridin-3-yl)oxy, (6-(cyano)pyridin-3-yl)oxy, (2-(cyano)pyridin-4-yl)oxy, (5-(cyano)pyridin-2-yl)oxy, (2-(chloro)pyridin-4-yl)oxy, pyrimidin-5-yloxy, pyrimidin-2-yloxy, thien-2-yloxy, and thien-3-yloxy.

The term "heteroaryloxyalkyl" means a heteroaryloxy group, as defined herein, appended to the parent molecular moiety through an alkyl group, as defined herein. Representative examples of heteroaryloxyalkyl include, but are not limited to, pyridin-3-yloxymethyl and 2-quinolin-3-yloxyethyl.

The term "heteroarylthio" means a heteroaryl group, as defined herein, appended to the parent molecular moiety through a sulfur atom. Representative examples of heteroarylthio include, but are not limited to, pyridin-3-ylthio and quinolin-3-ylthio.

The term "heteroarylthioalkyl" means a heteroarylthio group, as defined herein, appended to the parent molecular moiety through an alkyl group, as defined herein. Representative examples of heteroarylthioalkyl include, but are not limited to, pyridin-3-ylthiomethyl, and 2-quinolin-3-ylthioethyl.

The term "heterocycle" or "heterocyclic" means a monocyclic heterocycle, a bicyclic heterocycle or a tricyclic heterocycle. The monocyclic heterocycle is a 3-, 4-, 5-, 6- or 7-membered ring containing at least one heteroatom independently selected from the group consisting of O, N, and S. The 3- or 4-membered ring contains 1 heteroatom selected from the group consisting of O, N and S. The 5-membered ring contains zero or one double bond and one, two or three heteroatoms selected from the group consisting of O, N and S. The 6- or 7-membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a 5- or 6-membered monocyclic heterocycle fused to a phenyl group, or a 5- or 6-membered monocyclic heterocycle fused to a cycloalkyl, or a 5- or 6-membered monocyclic heterocycle fused to a cycloalkenyl, or a 5- or 6-membered monocyclic heterocycle fused to a monocyclic heterocycle. The bicyclic heterocycle is connected to the parent molecular moiety through any carbon atom or any nitrogen atom contained within the bicyclic heterocycle. Representative examples of bicyclic heterocycle include, but are not limited to, 1,3-benzodioxolyl, 1,3-benzodithiolyl, 2,3-dihydro-1,4-benzodioxinyl, benzodioxolyl, 2,3-dihydro-1-benzofuranyl, 2,3-dihydro-1-benzothienyl, chromenyl and 1,2,3,4-tetrahydroquinolinyl. The tricyclic heterocycle is a bicyclic heterocycle fused to a phenyl, or a bicyclic heterocycle fused to a cycloalkyl, or a bicyclic heterocycle fused to a cycloalkenyl, or a bicyclic heterocycle fused to a monocyclic heterocycle. The tricyclic heterocycle is connected to the parent molecular moiety through any carbon atom or any nitrogen atom contained within the tricyclic heterocycle. Representative examples of tricyclic heterocycle include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl.

The heterocycles of this invention are optionally substituted with 1, 2, 3 or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, oxo, —$NZ_1Z_2$ and ($NZ_3Z_4$)carbonyl.

The term "heterocyclealkoxy" means a heterocycle group, as defined herein, appended to the parent molecular moiety through an alkoxy group, as defined herein. Representative examples of heterocyclealkoxy include, but are not limited to, 2-pyridin-3-ylethoxy, 3-quinolin-3-ylpropoxy, and 5-pyridin-4-ylpentyloxy.

The term "heterocyclealkyl" means a heterocycle, as defined herein, appended to the parent molecular moiety through an alkyl group, as defined herein.

The term "heterocyclealkylcarbonyl" means a heterocyclealkyl, as defined herein, appended to the parent molecular moiety through a carbonyl group, as defined herein. Representative examples of heterocyclealkylcarbonyl include, but are not limited to, piperidin-4-ylmethylcarbonyl, piperazin-1-ylmethylcarbonyl, 3-methyl-1-pyrrolidin-1-ylbutylcarbonyl, (1R)-3-methyl-1-pyrrolidin-1-ylbutylcarbonyl, (1S)-3-methyl-1-pyrrolidin-1-ylbutylcarbonyl.

The term "heterocyclealkylthio" means a heterocyclealkyl group, as defined herein, appended to the parent molecular moiety through a sulfur atom. Representative examples of heterocyclealkylthio include, but are not limited to, 2-pyridin-3-ylethylthio, 3-quinolin-3-ylpropythio, and 5-pyridin-4-ylpentylthio.

The term "heterocyclecarbonyl" means a heterocycle, as defined herein, appended to the parent molecular moiety through a carbonyl group, as defined herein.

The term "heterocyclecarbonylalkyl" means a heterocyclecarbonyl, as defined herein, appended to the parent molecular moiety through an alkyl group, as defined herein.

The term "heterocycleoxy" means a heterocycle group, as defined herein, appended to the parent molecular moiety through an oxygen atom. Representative examples of heterocycleoxy include, but are not limited to, pyridin-3-yloxy and quinolin-3-yloxy.

The term "heterocycleoxyalkyl" means a heterocycleoxy group, as defined herein, appended to the parent molecular moiety through an alkyl group, as defined herein. Representative examples of heterocycleoxyalkyl include, but are not limited to, pyridin-3-yloxymethyl and 2-quinolin-3-yloxyethyl.

The term "heterocyclethio" means a heterocycle group, as defined herein, appended to the parent molecular moiety through a sulfur atom. Representative examples of heterocyclethio include, but are not limited to, pyridin-3-ylthio and quinolin-3-ylthio.

The term "heterocyclethioalkyl" means a heterocyclethio group, as defined herein, appended to the parent molecular moiety through an alkyl group, as defined herein. Representative examples of heterocyclethioalkyl include, but are not limited to, pyridin-3-ylthiomethyl, and 2-quinolin-3-ylthioethyl.

The term "hydroxy" means an —OH group.

The term "hydroxyalkyl" means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "hydroxy-protecting group" or "O-protecting group" means a substituent that protects hydroxyl groups against undesirable reactions during synthetic procedures. Examples of hydroxy-protecting groups include, but are not limited to, substituted methyl ethers, for example, methoxymethyl, benzyloxymethyl, 2-methoxyethoxymethyl, 2-(trimethylsilyl)-ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates. Commonly used hydroxy-protecting groups are disclosed in T. W. Greene and P. G. M. Wuts, Protective Groups in Organic Synthesis, 3rd edition, John Wiley & Sons, New York (1999).

The term "lower alkenyl" is a subset of alkenyl, as defined herein, and means an alkenyl group containing from 2 to 4 carbon atoms. Examples of lower alkenyl are ethenyl, propenyl, and butenyl.

The term "lower alkoxy" is a subset of alkoxy, as defined herein, and means a lower alkyl group, as defined herein, appended to the parent molecular moiety through an oxygen atom, as defined herein. Representative examples of lower alkoxy include, but are not limited to, methoxy, ethoxy, propoxy, 2-propoxy, butoxy, and tert-butoxy.

The term "lower alkyl" is a subset of alkyl as defined herein and means a straight or branched chain hydrocarbon group containing from 1 to 4 carbon atoms. Examples of lower alkyl are methyl, ethyl, n-propyl, iso-propyl, n-butyl, iso-butyl, sec-butyl, and tert-butyl.

The term "lower alkylthio" is a subset of alkylthio, means a lower alkyl group, as defined herein, appended to the parent molecular moiety through a sulfur atom. Representative examples of lower alkylthio include, but are not limited, methylthio, ethylthio, and tert-butylthio.

The term "lower alkynyl" is a subset of alkynyl, as defined herein, and means an alkynyl group containing from 2 to 4 carbon atoms. Examples of lower alkynyl are ethynyl, propynyl, and butynyl.

The term "lower haloalkoxy" is a subset of haloalkoxy, as defined herein, and means a straight or branched chain haloalkoxy group containing from 1 to 4 carbon atoms. Representative examples of lower haloalkoxy include, but are not limited to, trifluoromethoxy, trichloromethoxy, dichloromethoxy, fluoromethoxy, and pentafluoroethoxy.

The term "lower haloalkyl" is a subset of haloalkyl, as defined herein, and means a straight or branched chain haloalkyl group containing from 1 to 4 carbon atoms. Representative examples of lower haloalkyl include, but are not limited to, trifluoromethyl, trichloromethyl, dichloromethyl, fluoromethyl, and pentafluoroethyl.

The term "mercapto" means a —SH group.

The term "mercaptoalkyl" means a mercapto group, as defined herein, appended to the parent molecular moiety through an alkyl group, as defined herein. Representative examples of mercaptoalkyl include, but are not limited to, 2-mercaptoethyl and 3-mercaptopropyl.

The term "methylenedioxy" means an —OCH$_2$O— group wherein the oxygen atoms of the methylenedioxy are attached to the parent molecular moiety through two adjacent carbon atoms.

The term "nitrogen protecting group" means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl). Commonly used nitrogen protecting groups are disclosed in T. W. Greene and P. G. M. Wuts, Protective Groups in Organic Synthesis, 3rd edition, John Wiley & Sons, New York (1999).

The term "nitro" means a —NO$_2$ group.

The term "NZ$_1$Z$_2$" means two groups, Z$_1$ and Z$_2$, which are appended to the parent molecular moiety through a nitrogen atom. Z$_1$ and Z$_2$ are each independently selected from the group consisting of hydrogen, alkyl, alkylcarbonyl, alkoxycarbonyl, aryl, arylalkyl, formyl and (NZ$_5$Z$_6$)carbonyl. In certain instances within the invention, Z$_1$ and Z$_2$ taken together with the nitrogen atom to which they are attached form a heterocyclic ring. Representative examples of NZ$_1$Z$_2$ include, but are not limited to, amino, methylamino, acetylamino, acetylmethylamino, phenylamino, benzylamino, azetidinyl, pyrrolidinyl and piperidinyl.

The term "NZ$_3$Z$_4$" means two groups, Z$_3$ and Z$_4$, which are appended to the parent molecular moiety through a nitrogen atom. Z$_3$ and Z$_4$ are each independently selected from the group consisting of hydrogen, alkyl, aryl and arylalkyl. Representative examples of NZ$_3$Z$_4$ include, but are not limited to, amino, methylamino, phenylamino and benzylamino.

The term "NZ$_5$Z$_6$" means two groups, Z$_5$ and Z$_6$, which are appended to the parent molecular moiety through a nitrogen atom. Z$_5$ and Z$_6$ are each independently selected from the group consisting of hydrogen, alkyl, aryl and arylalkyl. Representative examples of NZ$_5$Z$_6$ include, but are not limited to, amino, methylamino, phenylamino and benzylamino.

The term "(NZ$_3$Z$_4$)carbonyl" means a NZ$_3$Z$_4$ group, as defined herein, appended to the parent molecular moiety through a carbonyl group, as defined herein. Representative examples of (NZ$_3$Z$_4$)carbonyl include, but are not limited to, aminocarbonyl, (methylamino)carbonyl, (dimethylamino)carbonyl, and (ethylmethylamino)carbonyl.

The term "oxo" means a =O moiety.

The term "sulfinyl" means a —S(=O)— group.

The term "sulfonyl" means a —SO$_2$— group.

The term "tautomer" means a proton shift from one atom of a compound to another atom of the same compound wherein two or more structurally distinct compounds are in equilibrium with each other.

Although typically it may be recognized that an asterisk is used to indicate that the exact subunit composition of a receptor is uncertain, for example α3b4* indicates a receptor that contains the α3 and β4 proteins in combination with other subunits, the term α7 as used herein is intended to include receptors wherein the exact subunit composition is both certain and uncertain. For example, as used herein α7 includes homomeric (α7)$_5$ receptors and α7* receptors, which denote a nAChR containing at least one α7 subunit.

The compounds of the invention can be used in the form of pharmaceutically acceptable salts, esters, or amides derived from inorganic or organic acids. "Pharmaceutically acceptable salts, esters and amides, include salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

"Pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. The salts can be prepared in situ during the final isolation and purification of the compounds of the invention or separately by reacting a free base function with a suitable organic acid.

Representative acid addition salts include, but are not limited to, acetate, adipate, alginate, citrate, aspartate, benzoate, benzenesulfonate, bisulfate, butyrate, camphorate, camphorsulfonate, digluconate, fumarate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Basic nitrogen-containing groups can be quaternized with such agents as lower alkyl halides, such as methyl, ethyl, propyl, and butyl chlorides, bromides and iodides; dialkyl sulfates, such as dimethyl, diethyl, dibutyl and diamyl sulfates; long chain halides, such as decyl, lauryl, myristyl and stearyl chlorides, bromides and iodides; arylalkyl halides, such as benzyl and phenethyl bromides and others. Water or oil-soluble or dispersible products are thereby obtained.

Examples of acids that can be used to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of the invention by reacting a carboxylic acid-containing moiety with a suitable base, such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals, such as lithium, sodium, potassium, calcium, magnesium, and aluminum salts, and the like; and nontoxic quaternary ammonia and amine cations, including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, and piperazine.

The term "pharmaceutically acceptable ester" refers to esters of compounds of the invention that hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) can be prepared according to conventional methods. Pharmaceutically acceptable esters can be appended onto hydroxy groups by reaction of the compound that contains the hydroxy group with acid and an alkylcarboxylic acid, such as acetic acid, or with acid and an arylcarboxylic acid, such as benzoic acid. In the case of compounds containing carboxylic acid groups, the pharmaceutically acceptable esters are prepared from compounds containing the carboxylic acid groups by reacting the compound with base, such as triethylamine, and an alkyl halide, alkyl triflate, for example, with methyl iodide, benzyl iodide, cyclopentyl iodide. They also can be prepared by reacting the compound with an acid, such as hydrochloric acid, and an alkylcarboxylic acid, such as acetic acid, or with acid and an arylcarboxylic acid, such as benzoic acid.

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) can be prepared according to conventional methods. Pharmaceutically acceptable amides can be prepared from compounds containing primary or secondary amine groups by reacting the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reacting the compound with base, such as triethylamine, a dehydrating agent, such as dicyclohexyl carbodiimide or carbonyl diimidazole, and an alkyl amine, dialkylamine, for example, with methylamine, diethylamine, piperidine. They also can be prepared by reacting the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds of formula (I).

Compounds of the Invention

Compounds of the invention have the formula (I):

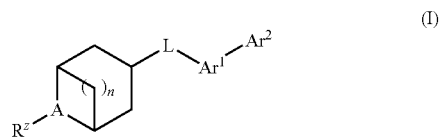

More particularly, compounds of formula (I) can include, but are not limited to, compounds wherein $R^z$ is H or alkyl, A is N, and n is 1 or 2. Certain preferred compounds exist wherein $R^z$ is H or methyl, A is N; L is O; and n is 2.

More particularly, in compounds of formula (I), $Ar^1$ is selected from:

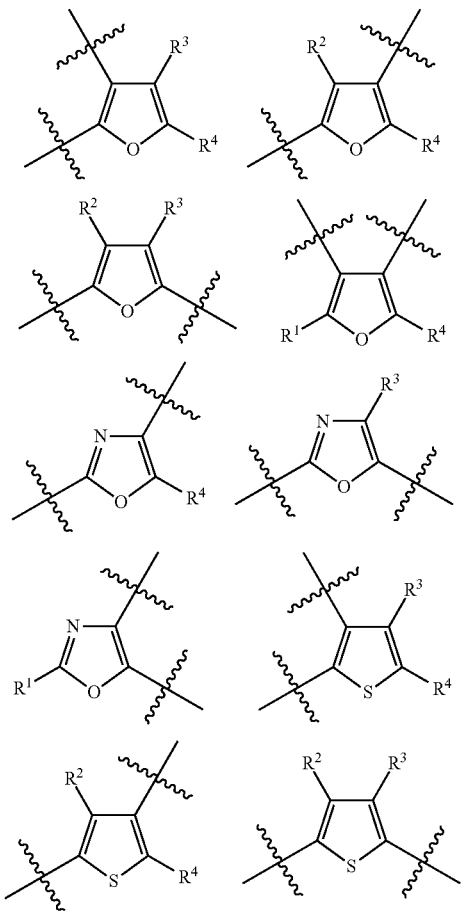

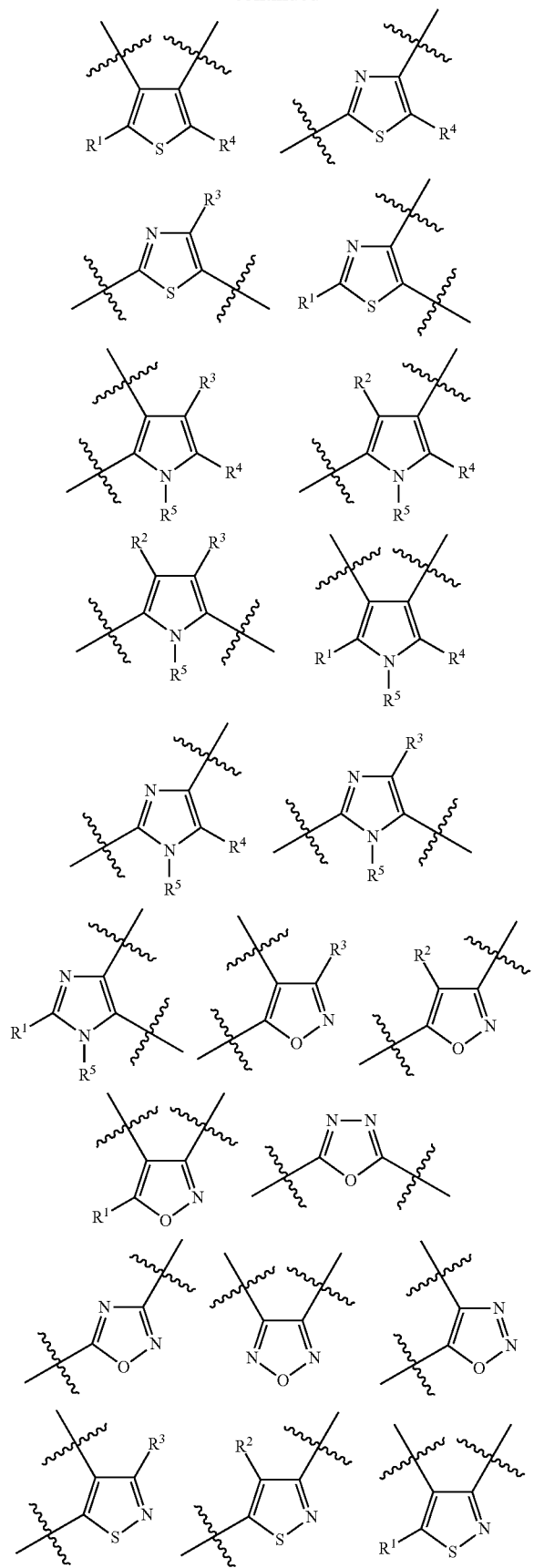
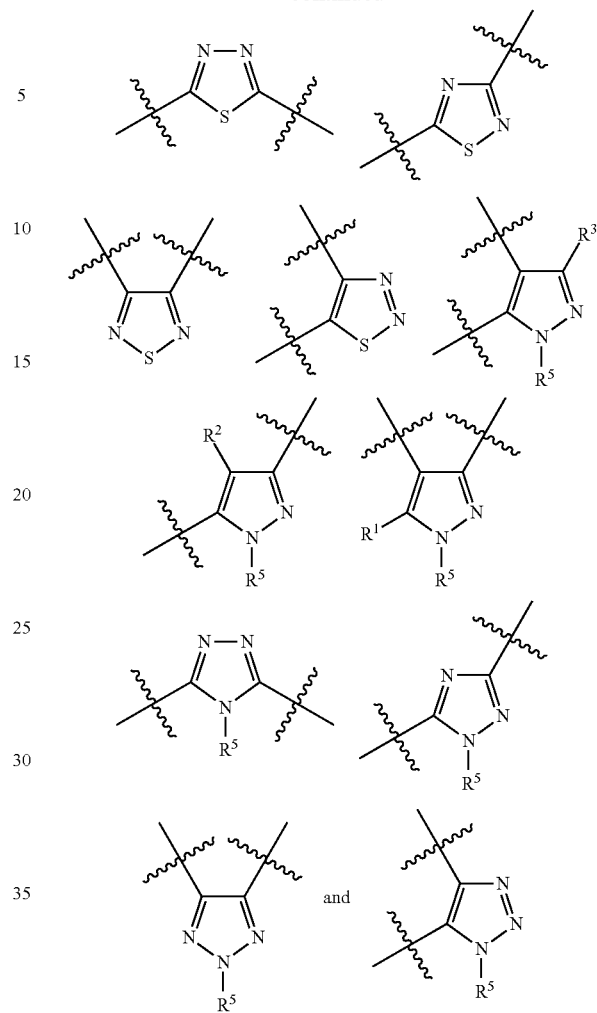

Wherein $R^1$, $R^2$, $R^3$ and $R^4$ are independently selected from hydrogen, acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amino, carboxy, cyano, formyl, haloalkoxy, haloalkyl, halo, hydroxy, hydroxyalkyl, mercapto, nitro, thioalkoxy, —$NR_gR_j$, ($NR_gR_j$)alkyl, ($NR_gR_j$)alkoxy, ($NR_gR_j$)carbonyl, and ($NR_gR_j$)sulfonyl;

$R^5$ is each independently selected from hydrogen, acyl, alkyl, and alkylsulfonyl; and $R_g$ and $R_j$ are each independently hydrogen or alkyl, or alkylcarbonyl.

More particularly, $Ar^1$ is

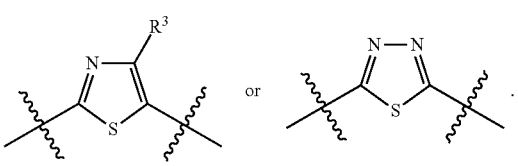

Most particularly, the invention includes, but is not limited to, compounds of formula (I) wherein A is N; R is H or methyl; L is O; n is 2; and $Ar^1$ is

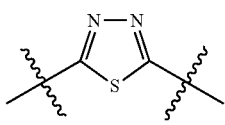

Compounds of formula (I) contain Ar² that is

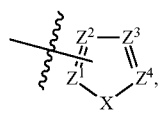
(i)

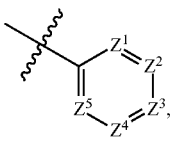
(ii)

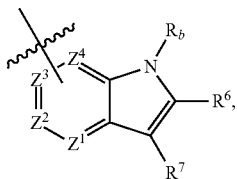
(iii)

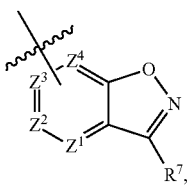
(iv)

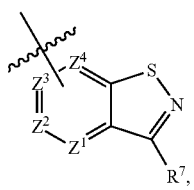
(v)

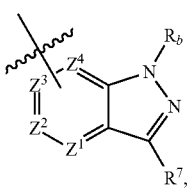
(vi)

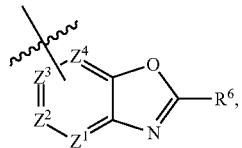
(vii)

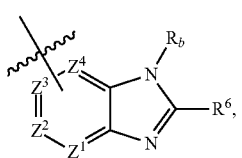
(viii)

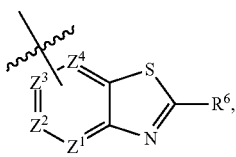
(ix)

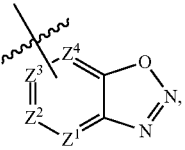
(x)

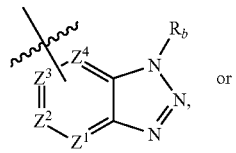
(xi)

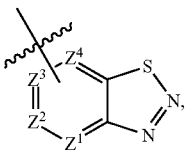
(xii)

wherein X is selected from the group consisting of O, S, and —N($R_a$)—; $Z^1$, $Z^2$, $Z^3$, $Z^4$ and $Z^5$ are each independently nitrogen or carbon, wherein the carbon atom is optionally substituted with a substituent selected from the group consisting of hydrogen, halogen, alkyl, —$OR_c$, -alkyl-$OR_c$, —$NR_dR_e$, and -alkyl-$NR_dR_e$.

$R^6$ and $R^7$ are each independently selected from the group consisting of hydrogen, alkenyl, alkoxy, alkoxyalkoxy, alkoxyalkyl, alkoxycarbonyl, alkoxyimino, alkoxysulfonyl, alkyl, alkylcarbonyl, alkylcarbonyloxy, alkylsulfonyl, alkynyl, carboxy, cyano, formyl, haloalkoxy, haloalkyl, halo, hydrogen, hydroxy, hydroxyalkyl, mercapto, nitro, thioalkoxy, —$NR_fR_g$, ($NR_fR_g$)alkyl, ($NR_fR_g$)alkoxy, ($NR_fR_g$)carbonyl, and ($NR_fR_g$)sulfonyl; provided that when $R^6$ or $R^7$ is hydroxy, the corresponding tautomers are allowed. $R_a$, $R_b$, $R_c$, $R_d$, $R_e$, $R_f$, and $R_g$ are each independently selected from the group consisting of hydrogen and alkyl, alkylcarbonyl. $R^z$ is selected from hydrogen, alkyl, cycloalkylalkyl, and arylalkyl. Preferred compounds are disclosed wherein $R^z$ is hydrogen or alkyl. Preferably, $R^z$ is H or methyl.

Preferred compounds are disclosed, wherein Ar² is

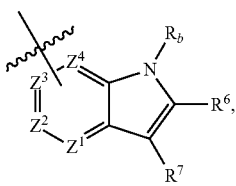
(iii)

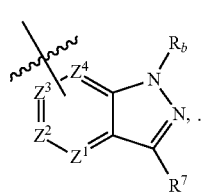

wherein $Z^1$, $Z^2$, $Z^3$, $Z^4$, $R_b$, $R^6$ and $R^7$ are as previously defined. More preferably $Ar^2$ is the molecule of formula (iii).

Most particularly, the invention relates to compounds of formula (I) wherein A is N; $R^z$ is methyl; L is O; n is 2; $Ar^1$ is

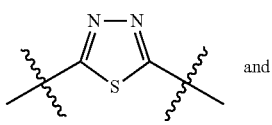 [SMILES: *c1nnc(*)s1]

and $Ar^2$ is

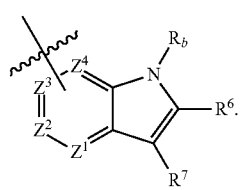

Compounds for the method of the invention, including but not limited to those specified in the examples or otherwise specifically named, can modulate, and often possess an affinity for, nAChRs, and more particularly α7 nAChRs. As α7 nAChRs ligands, the compounds of the invention are useful for the treatment or prevention of α7 nAChR-mediated diseases or conditions.

Specific examples of compounds useful for the treatment or prevention of α7 nAChR-mediated diseases or conditions include, but are not limited to:

2-[(endo)-8-Methyl-8-azabicyclo[3.2.1]octan-3-yloxy]-5-(1H-indol-5-yl)-thiazole;
2-[(endo)-8-Methyl-8-azabicyclo[3.2.1]octan-3-yloxy]-5-phenyl-thiazole;
2-[(endo)-8-Methyl-8-azabicyclo[3.2.1]octan-3-yloxy)-5-(pyridin-3-yl]-thiazole;
5-(1H-indol-6-yl)-2-[(endo)-8-methyl-8-azabicyclo[3.2.1]octan-3-yloxy]thiazole;
5-(1H-indol-4-yl)-2-[(endo)-8-methyl-8-azabicyclo[3.2.1]octan-3-yloxy]thiazole;
5-(Benzofuran-5-yl)-2-[(endo)-8-methyl-8-azabicyclo[3.2.1]octan-3-yloxy]thiazole;
5-(Benzo[b]thiophen-5-yl)-2-[(endo)-8-methyl-8-azabicyclo[3.2.1]octan-3-yloxy]thiazole;
5-(2-(Trifluoromethyl)-1H-indol-5-yl)-2-[(endo)-8-methyl-8-azabicyclo[3.2.1]octan-3-yloxy])thiazole;
5-(Dibenzo[b,d]thiophen-2-yl)-2-[(endo)-8-methyl-8-azabicyclo[3.2.1]octan-3-yloxy]thiazole;
2-[(exo)-8-Methyl-8-azabicyclo[3.2.1]octan-3-yloxy]-5-(1H-indol-5-yl)-thiazole;
2-[(exo)-8-Methyl-8-azabicyclo[3.2.1]octan-3-yloxy]-5-(1H-indol-6-yl)-thiazole;
2-[(exo)-8-Methyl-8-azabicyclo[3.2.1]octan-3-yloxy]-5-phenyl-thiazole;
2-[(exo)-8-Methyl-8-azabicyclo[3.2.1]octan-3-yloxy]-5-(pyridin-3-yl)-thiazole;
2-[(endo)-8-Methyl-8-azabicyclo[3.2.1]octan-3-yloxy]-5-phenyl-1,3,4-thiadiazole;
2-(1H-Indol-5-yl)-5-[(endo)-8-methyl-8-azabicyclo[3.2.1]octan-3-yloxy]-1,3,4-thiadiazole;
2-(Benzofuran-5-yl)-5-[(endo)-8-methyl-8-azabicyclo[3.2.1]octan-3-yloxy)-1,3,4-thiadiazole;
2-(Benzo[b]thiophen-5-yl)-5-[(endo)-8-methyl-8-azabicyclo[3.2.1]octan-3-yloxy]-1,3,4-thiadiazole;
2-(3-Fluorophenyl)-5-[(endo)-8-methyl-8-azabicyclo[3.2.1]octan-3-yloxy]-1,3,4-thiadiazole;
2-[(endo)-8-Methyl-8-azabicyclo[3.2.1]octan-3-yloxy]-5-m-tolyl-1,3,4-thiadiazole;
2-(4-Fluorophenyl)-5-[(endo)-8-methyl-8-azabicyclo[3.2.1]octan-3-yloxy]-1,3,4-thiadiazole;
2-(3-Chlorophenyl)-5-[(endo)-8-methyl-8-azabicyclo[3.2.1]octan-3-yloxy]-1,3,4-thiadiazole;
2-(1H-Indol-6-yl)-5-[(endo)-8-methyl-8-azabicyclo[3.2.1]octan-3-yloxy]-1,3,4-thiadiazole;
2-(1H-indol-4-yl)-5-[(endo)-8-methyl-8-azabicyclo[3.2.1]octan-3-yloxy]-1,3,4-thiadiazole;
2-(3-Cyanophenyl)-5-[(endo)-8-methyl-8-azabicyclo[3.2.1]octan-3-yloxy]-1,3,4-thiadiazole;
2-(3-Trifluoromethylphenyl)-5-[(endo)-8-methyl-8-azabicyclo[3.2.1]octan-3-yloxy)-1,3,4-thiadiazole;
2-(4-Chlorophenyl)-5-((1R,3R,5S)-8-methyl-8-azabicyclo[3.2.1]octan-3-yloxy)-1,3,4-thiadiazole;
2-(2-(Trifluoromethyl)-1H-indol-5-yl)-5-[(endo)-8-methyl-8-azabicyclo[3.2.1]octan-3-yloxy]-1,3,4-thiadiazole;
2-(3-Chloro-4-fluorophenyl)-5-[(endo)-8-methyl-8-azabicyclo[3.2.1]octan-3-yloxy]-1,3,4-thiadiazole;
2-(4-(Trifluoromethyl)phenyl)-5-[(endo)-8-methyl-8-azabicyclo[3.2.1]octan-3-yloxy]-1,3,4-thiadiazole;
2-(4-Methoxyphenyl)-5-[(endo)-8-methyl-8-azabicyclo[3.2.1]octan-3-yloxy]-1,3,4-thiadiazole;
2-(3-Aminophenyl)-5-[(endo)-8-methyl-8-azabicyclo[3.2.1]octan-3-yloxy]-1,3,4-thiadiazole;
2-(4-Ethylphenyl)-5-[(endo)-8-methyl-8-azabicyclo[3.2.1]octan-3-yloxy]-1,3,4-thiadiazole;
2-(4-Acetylphenyl)-5-[(endo)-8-methyl-8-azabicyclo[3.2.1]octan-3-yloxy]-1,3,4-thiadiazole; and
N-[(endo)-8-Methyl-8-azabicyclo[3.2.1]octan-3-yl]-5-phenyl-1,3,4-thiadiazol-2-amine;

or pharmaceutically acceptable salts, esters, amides, and prodrugs thereof.

Compound names are assigned by using AutoNom naming software, which is provided by MDL Information Systems GmbH (formerly known as Beilstein Informationssysteme) of Frankfurt, Germany, and is part of the CHEMDRAW® ULTRA v. 6.0.2 software suite (Cambridge Soft. Cambridge, Mass.).

Compounds of the invention can exist as stereoisomers wherein asymmetric or chiral centers are present. These stereoisomers are "R" or "S" depending on the configuration of substituents around the chiral element. The terms "R" and "S" used herein are configurations as defined in IUPAC 1974 Recommendations for Section E, Fundamental Stereochemistry, Pure Appl. Chem., 1976, 45: 13-30. The attachment of L to the azabicyclic alkane may be considered to encompass both the endo and exo geometries. The invention contemplates various stereoisomers and mixtures thereof and is specifically included within the scope of this invention. Stereoisomers include enantiomers and diastereomers, and mixtures of enantiomers or diastereomers. Individual stereoisomers of compounds of the invention can be prepared synthetically from commercially available starting materials that contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Methods for Preparing Compounds of the Invention

The reactions exemplified in the schemes are performed in a solvent appropriate to the reagents and materials used and suitable for the transformations being effected. The described transformations may require modifying the order of the synthetic steps or selecting one particular process scheme over another in order to obtain a desired compound of the invention, depending on the functionality present on the molecule.

The methods described below can entail use of various enantiomers. Where the stereochemistry is shown in the Schemes, it is intended for illustrative purposes only.

4, 973, provide compounds of formula (3). Compounds of formula (3) when treated with hexamethylditin or an organoborane compound of formula (4), such as bis(pinacolato)diboron or bis(catecholato)diboron, wherein $R^m$ is hydrogen, alkyl or aryl, in the presence of a palladium catalyst, such as, but not limited to, $Pd(OAc)_2$, $PdCl_2(PPh_3)_2$, $Pd(PPh_3)_4$, $PdCl_2(dppf)$, $Pd_2(dba)_3$ provide the corresponding tin or boronic acid/esters of formula (5), wherein M is $-Sn-(Me)_3$ or $-B(OR^m)_2$. Compounds of formula (5) when treated with compounds of formula (6), wherein $Ar^2$ is an aryl or heteroaryl ring and halo is bromide, chloride, or iodide, in the presence of a palladium catalyst, such as, but not limited to, $Pd(OAc)_2$, $PdCl_2(PPh_3)_2$, $Pd(PPh_3)_4$, $PdCl_2(dppf)$, $Pd_2(dba)_3$, will provide compounds of formula (8). Alternatively, compounds of formula (6) when treated with hexamethylditin or a di-borane containing compound of formula (4), such as bis(pinacolato)diboron and bis(catecholato)diboron, in the presence of a palladium catalyst provide a organotin or orga-

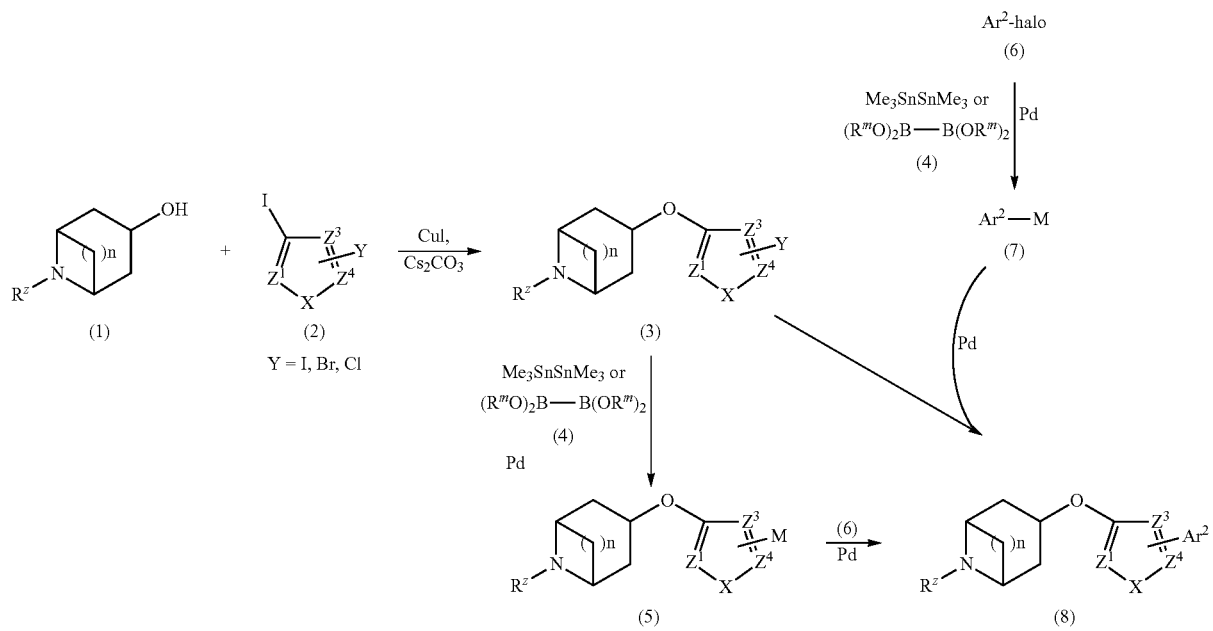

Scheme 1

Compounds of formula (8), wherein $Ar^2$ are as defined in formula (I), can be prepared as described in Scheme 1. Compounds of formula (1) when treated with a compound of formula (2), wherein X is oxygen, sulfur or nitrogen; Y is bromide, chloride, or iodide, in the presence of CuI, 1,10-phenanthroline and $Cs_2CO_3$ in a solvent such as, but not limited to, toluene at 110° C. as described in Org. Lett., 2002, noboronic acid/esters containing compounds of formula (7), wherein $Ar^2$ is a bicyclic heteroaryl and wherein M is $-Sn-(Me)_3$ or $-B(OR^m)_2$. Compounds of formula (7) when treated with a compound of formula (3) in the presence of a palladium catalyst, such as, but not limited to, $Pd(OAc)_2$, $PdCl_2(PPh_3)_2$, $Pd(PPh_3)_4$, $PdCl_2(dppf)$, $Pd_2(dba)_3$, provide a compound of formula (8).

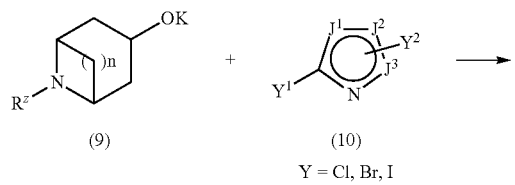

Scheme 2

-continued

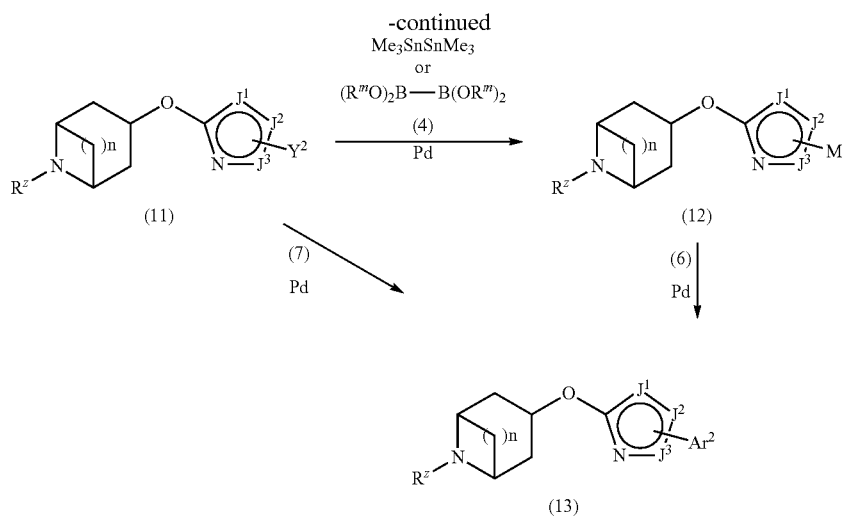

Compounds of formula (13), wherein Ar¹ is a nitrogen-containing heteroaryl, for example, imidazoles, oxazoles, thiazoles, oxadiazoles, thiadiazoles and triazoles; and Ar² is as defined in formula (I), can be prepared as shown in Scheme 2. Compounds of formula (9), wherein $R^z$ is as previously defined and K represents the potassium, which are prepared by treating hydroxyl containing heterocycles of similar formula with potassium tert-butoxide in solvents such as, but not limited to, THF DME, or DMF to provide the potassium oxide containing compounds of formula (9). The compounds of formula (9) when treated with compounds of formula (10), wherein $Y^1$ is bromo, chloro or iodo, $Y^2$ is bromo, chloro, iodo, or Ar²; and $J^1$, $J^2$ and $J^3$ are independently either carbon or nitrogen, sulfur and oxygen, such as, but not limited to, 2,5-dibromothiazole and 2,5-dibromo-1,3,4-thiadiazole, provide compounds of formula (11). When $Y^2$ is Ar², compounds of formula (11) are preferred embodiments. When $Y^2$ is a halogen, compounds of formula (11) when treated with hexamethylditin or a di-borane containing compound of formula (4) in the presence of a palladium catalyst according to the procedure outlined in Scheme 1 provide the compounds of formula (12). Compounds of formula (12) treated with compounds of formula (6) in the presence of a palladium catalyst, such as, but not limited to, $Pd(OAc)_2$, $PdCl_2(PPh_3)_2$, $Pd(PPh_3)_4$, $PdCl_2(dppf)$, $Pd_2(dba)_3$, provide compounds of formula (13). Alternatively, the compounds of formula (11) when treated with organo stannane or organo boronic acid containing compounds of formula (7), as described in Scheme 1, in the presence of a palladium catalyst, such as, but not limited to, $Pd(OAc)_2$, $PdCl_2(PPh_3)_2$, $Pd(PPh_3)_4$, $PdCl_2$(dppf), $Pd_2(dba)_3$, provide a compound of formula (13).

Alternatively, compounds of formula (8) may be prepared as outlined in Scheme 3. Compounds of formula (1) when treated with a compound of formula (14), wherein X is oxygen, sulfur or nitrogen; $Z^1$, $Z^3$ and $Z^4$ is nitrogen or carbon, Y is bromo, chloro, iodo or is Ar², in the presence of but not limited to, diethyl azodicarboxylate or diisopropyl azodicarboxylate and a phosphine, such as triphenylphosphine, provide compounds of formula (15). When Y is Ar², compounds of formula (15) are preferred embodiments. When Y is a halogen, the further treatment of the compound according to conditions outlined in Schemes 1-2 provide compounds of formula (8) which are preferred embodiments.

Scheme 4

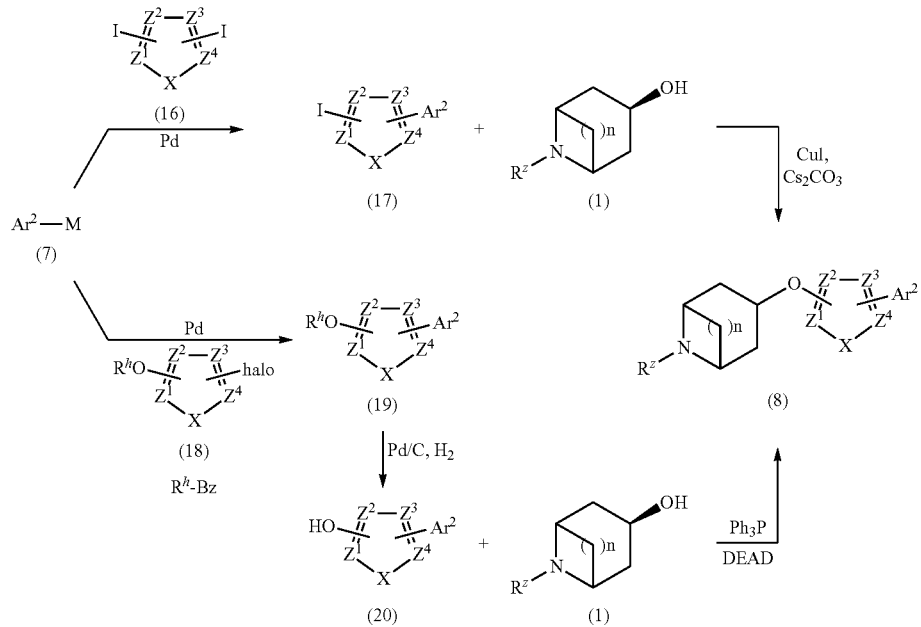

Another method of generating compounds of formula (8) is described in Scheme 4. The tin or boronic acid/esters compounds of formula (7) can be coupled with a variety of hetreoaryl halides that provides a method of generating biaryl compounds of formula (17) and compounds of formula (20). For example, compounds of formula (7) when treated with the compounds of formula (16) in the presence of a palladium catalyst, such as, but not limited to, $Pd(OAc)_2$, $PdCl_2(PPh_3)_2$, $Pd(PPh_3)_4$, $PdCl_2(dppf)$, $Pd_2(dba)_3$, provide compounds of formula (17). Compounds of formula (17) when treated with compounds of formula (1) in the presence of copper(I) iodide and cesium carbonate and 1,10-phenanthroline as described in scheme 1, provide compounds of formula (8). Alternatively, compounds of formula (7) when treated with a compound of formula (18), wherein $R^a$ is benzyl or another appropriate alcohol protecting group as known to one skilled in the art, in the presence of a palladium catalyst provide compounds of formula (19). The deprotection of the alcohol protecting group, for example when $R^h$ is benzyl, is generally achieved using palladium on carbon and an atmosphere of hydrogen to provide compounds of formula (20). Compounds of formula (20) when treated with compounds of formula (1) in the presence of triphenylphosphine and diethyldiazocarboxylate or a similar reagent provide compounds of formula (8).

Scheme 5

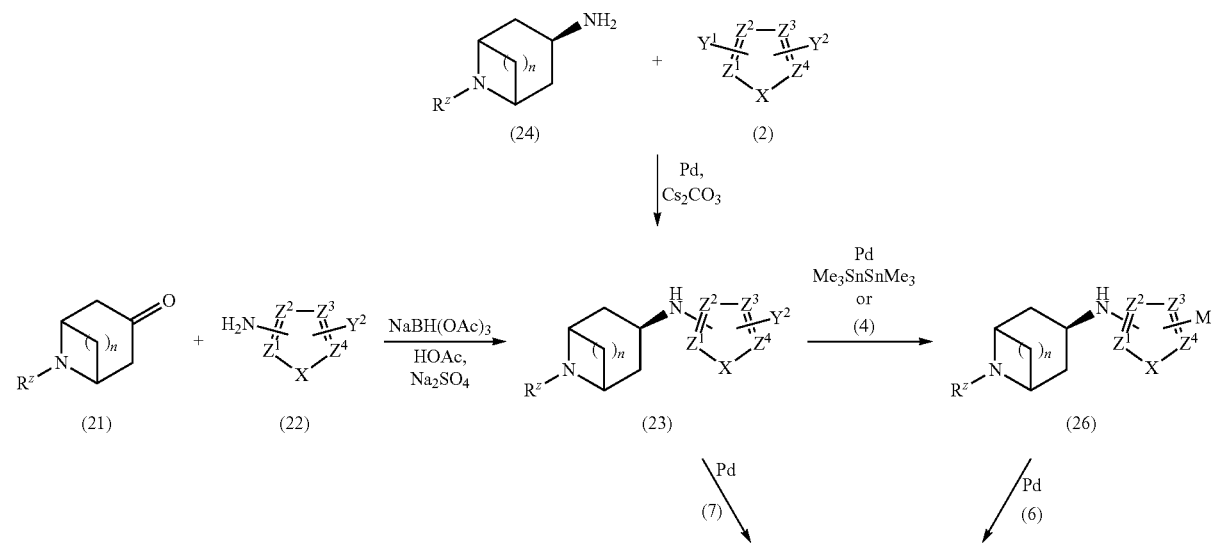

-continued

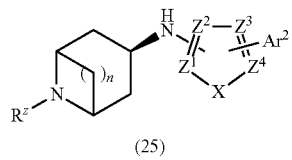

(25)

Compounds of formula (25), which are representative of compounds of formula (I), wherein L is —NH—, can be prepared as shown in Scheme 5. Compounds of formula (21) when treated with compounds of formula (22), wherein $Y^2$ is bromide, chloride, iodide, or $Ar^2$; along with sodium triacetoxy borohydride and $Na_2SO_4$ in acetic acid provide compounds of formula (23). Alternatively, a compound of formula (23) can be obtained by treating compounds of formula (24) with a compound of formula (2), wherein $Y^1$ is chloro, bromo or iodo and $Y^2$ is bromide, chloride, iodide, or $Ar^2$; in the presence of a palladium catalyst, such as, but not limited to, $Pd(OAc)_2$, $PdCl_2(PPh_3)_2$, $Pd(PPh_3)_4$, $PdCl_2(dppf)$, $Pd_2(dba)_3$, preferably in toluene. When $Y^2$ is $Ar^2$, compounds of formula (23) are representative of the present invention. When $Y^2$ is a halogen, the further treatment of the compound of formula (23) with a tin or diboron of formula (4), such as bis(pinacolato)diboron and bis(catecholato)diboron, under conditions described in Scheme 2, provide the corresponding tin or boronic acid/ester compounds of formula (26). Compounds of formula (26) when treated with a compound of formula (6) in the presence of a palladium catalyst, provide the compound of formula (25). Alternatively, the compound of formula (23) when treated with a tin or boronic acid/ester containing compound of formula (7) in the presence of a palladium catalyst also provide compounds of formula (25).

of compounds of formula (I) wherein L is S. Alternatively, the compound of formula (28) when treated with a hexamethylditin or diboron reagent of formula (4), such as bis(pinacolato)diboron and bis(catecholato)diboron, in the presence of a palladium catalyst provide a compound of formula (29). Compounds of formula (29) when treated with compounds of formula (6), wherein halo is bromo, chloro or iodo, in the presence of a palladium catalyst provide compounds of formula (30).

In addition, compounds of formula (I) wherein A is N can be converted to compounds of formula (I) wherein A is $N^+$—$O^-$ by treatment with an oxidizing agent. Examples of the oxidizing agent include, but are not limited to, aqueous hydrogen peroxide and m-chloroperbenzoic acid. The reaction is generally performed in a solvent such as, but not limited to, acetonitrile, water, dichloromethane, acetone or mixture thereof, preferably a mixture of acetonitrile and water, at a temperature from about 0° C. to about 80° C., for a period of about 1 hour to about 4 days.

The compounds and intermediates of the invention can be isolated and purified by methods well known to those skilled in the art of organic synthesis. Examples of conventional methods for isolating and purifying compounds can include, but are not limited to, chromatography on solid supports, such as silica gel, alumina, or silica derivatized with alkylsilane Scheme 6

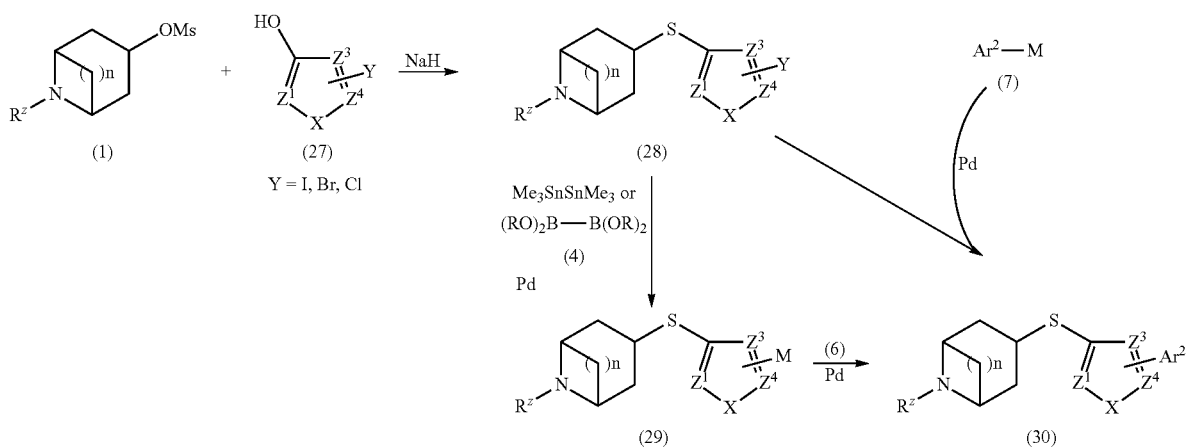

Compounds of formula (30), wherein L is S, and $Ar^1$ and $Ar^2$ are as defined in formula (I), can be prepared as shown in Scheme 6. Compounds of formula (27), wherein Y is bromide, chloride, iodide, or $Ar^2$, when pretreated with sodium hydride in a solvent such as, but not limited to, DMF, followed by treatment with compounds of formula (1) provide compounds of formula (28). When Y is $Ar^2$, compounds of formula (28) are representative of the present invention. When Y is a halogen, further treatment of compounds of formula (28) with a compound of formula (7) as described in Scheme 1, provide compounds of formula (30), which are representative groups; by recrystallization at high or low temperature with an optional pretreatment with activated carbon; thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compounds of the invention have at least one basic nitrogen whereby the compound can be treated with an acid to form a desired salt. For example, a compound can be reacted with an acid at, or above, room temperature to provide the desired salt that is deposited and collected by filtration after cooling. Examples of acids suitable for the reaction include, but are not limited to, tartaric, lactic, succinic, as well as mandelic, atrolactic, methanesulfonic, ethanesulfonic, toluenesulfonic, naphthalenesulfonic, carbonic, fumaric, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

Nitrogen protecting groups can be used for protecting amine groups present in the described compounds. Such methods and some suitable nitrogen protecting groups are described in Greene and Wuts (Protective Groups In Organic Synthesis, Wiley and Sons, 1999). For example, suitable nitrogen protecting groups include, but are not limited to, tert-butoxycarbonyl (Boc), benzyloxycarbonyl (Cbz), benzyl (Bn), acetyl, and trifluoroacetyl. More particularly, the Boc protecting group can be removed by treatment with an acid such as trifluoroacetic acid or hydrochloric acid. The Cbz and Bn protecting groups may be removed by catalytic hydrogenation. The acetyl and trifluoroacetyl protecting groups can be removed by a hydroxide ion.

The compounds and processes of the invention can be better understood by reference to the following Examples, which are intended as an illustration, but not a limitation, of the scope of the invention.

Example 1

2-[(endo)-8-Methyl-8-azabicyclo[3.2.1]octan-3-yloxy]-5-(1H-indol-5-yl)-thiazole bis(hydrochloric acid)

Example 1A

5-Bromo-2-[(endo)-8-methyl-8-azabicyclo[3.2.1]octan-3-yloxy]thiazole

Tropine (Aldrich, 420 mg, 3.0 mmol) in THF (anhydrous, Aldrich, 20 mL) was treated with potassium tert-butoxide (Aldrich, 350 mg, 3.50 mmol) at ambient temperature for 1.0 hour. A solution of 2,5-dibromothiazole (Aldrich, 969 mg, 4.0 mmol) in THF (anhydrous, Aldrich, 10 mL) was added to the above solution at 10-20° C. The mixture was then stirred at ambient temperature for 3 hours. The mixture was quenched with water (1 mL) and concentrated under reduced pressure. The residue was diluted with $CHCl_3$ (100 mL) and washed with brine (2×10 mL). The organic solution was concentrated under reduced pressure and the residue was purified by chromatography ($SiO_2$, $CH_2Cl_2$/MeOH/$NH_3.H_2O$, v. 90/10/2, $R_f$=0.15) to give the title compound. $^1$H NMR (300 MHz, $CD_3OD$) δ ppm 2.00-2.12 (m, 8H), 2.36 (s, 3H), 3.17-3.29 (m, 2H), 5.10 (t, J=5.09 Hz, 1H), 7.12 (s, 1H); MS (DCI/$NH_3$) m/z 303 (M+1)$^+$, 305 (M+1)$^+$.

Example 1B

2-[(endo)-8-Methyl-8-azabicyclo[3.2.1]octan-3-yloxy]-5-(1H-indol-5-yl)-thiazole

A solution of the product of Example 1A (200 mg, 0.66 mmol), 5-indolyl boronic acid (Frontier, 160 mg, 1.0 mmol) and $K_2CO_3$ aqueous solution (2M, 1 mL) in the presence of $Pd(PPh_3)_4$ (15.3 mg, 0.013 mmol) in dioxane (4 mL) was heated to 80-90° C. for 10 hours. The mixture was cooled to ambient temperature and purified by chromatography ($SiO_2$, $CH_2Cl_2$/MeOH/$NH_3.H_2O$, v. 90/10/2, $R_f$=0.10) to give the title compound. $^1$H NMR (300 MHz, $CDCl_3$) δ ppm 1.99-2.16 (m, 6H), 2.18-2.30 (m, 2H), 2.33 (s, 3H), 3.12-3.18 (m, 2H), 5.16 (t, J=4.92 Hz, 1H), 6.58 (t, J=2.60 Hz, 1H), 7.23 (t, J=3.00 Hz, 1H), 7.31 (dd, J=8.40, 1.70 Hz, 1H), 7.39 (d, J=8.50 Hz, 1H), 7.69 (s, 1H), 8.22 [s (br.), 1H]; MS (DCI/$NH_3$) m/z 340 (M+1)$^+$.

Example 1C

2-[(endo)-8-Methyl-8-azabicyclo[3.2.1]octan-3-yloxy]-5-(1H-indol-5-yl)-thiazole bis(hydrochloric acid The product of Example 1B (210 mg, 0.62 mmol) was treated with HCl (Aldrich, 4 M in dioxane, 0.5 mL, 2.0 mmol) in EtOAc (5 mL) at ambient temperature for 10 hours. The precipitated solid was filtered and dried to give the title compound as a white solid. $^1$H NMR (300 MHz, Pyridine-$D_5$) δ ppm 2.03-2.38 (m, 8H), 2.79 (s, 3H), 3.74-3.93 (m, 2H), 5.39 (t, J=4.45 Hz, 1H), 6.77 (s, 1H), 7.55 (dd, J=8.44, 1.38 Hz, 1H), 7.57-7.62 (m, 1H), 7.64 (s, 1H), 7.70 (d, J=8.29 Hz, 1H), 8.05 (s, 1H), 12.37 [s (br.), 1H]; MS (DCI/$NH_3$) m/z 340 (M+1)$^+$. Anal. calcd. for $C_{14}H_{18}ClN_3.2.00HCl.1.40H_2O$: C, 52.15; H, 5.94; N, 9.60. Found: C, 51.89; H, 5.56; N, 9.22.

Example 2

2-[(endo)-8-Methyl-8-azabicyclo[3.2.1]octan-3-yloxy]-5-phenyl-thiazole hydrochloric acid Example 2A 2-[(endo)-8-Methyl-8-azabicyclo[3.2.1]octan-3-yloxy]-5-phenyl-thiazole The product of Example 1A (200 mg, 0.66 mmol) was coupled with phenyl boronic acid (Aldrich, 122 mg, 1.0 mmol) according to the procedure outlined in Example 1B. The title compound was purified by chromatography ($SiO_2$, $CH_2Cl_2$/MeOH/$NH_3.H_2O$, v. 90/10/2, $R_f$=0.20). $^1$H NMR (300 MHz, $CDCl_3$) δ ppm 2.13-2.44 (m, 8H), 2.63 (s, 3H), 3.40-3.71 (m, 2H), 5.28 (t, J=4.58 Hz, 1H), 7.28-7.59 (m, 6H); MS (DCI/$NH_3$) m/z 301 (M+1)$^+$.

Example 2B

2-[(endo)-8-Methyl-8-azabicyclo[3.2.1]octan-3-yloxy]-5-phenyl-thiazole hydrochloric acid The product of Example 2A (140 mg, 0.47 mmol) was treated with HCl (Aldrich, 4 M in dioxane, 0.5 mL, 2.0 mmol) in EtOAc (5 mL) at ambient temperature for 10 hours to give the title compound as a white solid. $^1$H NMR (300 MHz, $CD_3OD$) δ ppm 2.03-2.38 (m, 8H), 2.79 (s, 3H), 3.74-3.93 (m, 2H), 5.39 (t, 2.23-2.37 (m, 4H), 2.41-2.57 (m, 4H), 2.84 (s, 3H), 3.87-4.07 (m, 2H), 5.26 (t, J=3.45 Hz, 1H), 7.25-7.35 (m, 1H), 7.35-7.43 (m, 2H), 7.45-7.55 (m, 3H) MS (DCI/$NH_3$) m/z 301 (M+1)$^+$.

Example 3

2-[(endo)-8-Methyl-8-azabicyclo[3.2.1]octan-3-yloxy)-5-(pyridin-3-yl]-thiazole hydrochloric acid Example 3A 2-[(endo)-8-Methyl-8-azabicyclo[3.2.1]octan-3-yloxy]-5-(pyridin-3-yl)-thiazole The product of Example 1A (200 mg, 0.66 mmol) was coupled with 3-pyridinyl boronic acid (Aldrich, 123 mg, 1.0 mmol) according to the procedure outlined in Example 1B. The title compound was purified by chromatography (SiO₂, CH₂Cl₂/MeOH/NH₃.H₂O, v. 90/10/2, R$_f$=0.10). ¹H NMR (300 MHz, CDCl₃) δ ppm 2.14-2.50 (m, 6H), 2.66 (s, 3H), 2.80-3.10 (m, 2H), 3.54-3.78 (m, 2H), 5.32 (t, J=5.80 Hz, 1H), 7.31 (ddd, J=4.75, 1H), 7.37 (s, 1H), 7.72 (ddd, J=4.75, 8.20, 2.30, 1.70 Hz, 1H), 8.53 (dd, J=8.20, 4.70, 0.70 Hz, 1H), 8.70 (d, J=1.70 Hz, 1H); MS (DCI/NH₃) m/z 302 (M+1)⁺.

Example 3B

2-[(endo)-8-Methyl-8-azabicyclo[3.2.1]octan-3-yloxy)-5-(pyridin-3-yl)-thiazole hydrochloric acid The product of Example 3A (140 mg, 0.47 mmol) was treated with HCl (Aldrich, 4 M in dioxane, 0.5 mL, 2.0 mmol) in EtOAc (5 mL) at ambient temperature for 10 hours to give the title compound as a white solid. ¹H NMR (300 MHz, CD₃OD) δ ppm 2.23-2.65 (m, 8H), 2.85 (s, 3H), 3.87-4.04 (m, 2H), 5.39 (t, J=4.24 Hz, 1H), 7.92 (s, 1H), 8.11 (dd, J=8.14, 5.76 Hz, 1H), 8.72-8.82 (m, 2H), 9.13 (d, J=2.03 Hz, 1H); MS (DCI/NH₃) m/z 301 (M+1)⁺.

Example 4

5-(1H-Indol-6-yl)-2-[(endo)-8-methyl-8-azabicyclo[3.2.1]octan-3-yloxy]thiazole trifluoroacetate The mixture of the product of Example 1A (150 mg, 0.497 mmol), 6-indolyl boronic acid (Frontier, 158 mg, 0.981 mmol), bis(triphenylphosphine)palladium(II) chloride (Aldrich 7.0 mg, 0.01 mmol) and biphenyl-2-yl-dicyclohexylphosphane (Strem Chemicals, 10.5 mg, 0.03 mmol) in dioxane/EtOH/Na₂CO₃ (aq., 1 M) (v. 1/1/1 3 mL) were heated to 130° C. and microwaved at 300 watts for 15 minutes in an Emry™ Creator microwave. The solid was filtered with a syringe filter and the organic solution was directly purified by preparative HPLC (Gilson, column, Xterra® 5 µm, 40×100 mm. eluting solvents, MeCN/H₂O containing 0.1% v. TFA (90% to 10% over 25 minutes, flow rate of 40 mL/minute, uv, 254 nm). The fractions containing the desired product were collected and concentrated under reduced pressure. The residue was stirred in ether/ethanol (v. 10/1, 5 mL) at ambient temperature for 16 hours to provide the title compound. ¹H NMR (300 MHz, CD₃OD) δ ppm 2.33-2.57 (m, 8H), 2.84 (s, 3H), 3.85-3.98 (m, 2H), 5.25 (t, J=4.24 Hz, 1H), 6.45 (dd, J=2.4, 0.7 Hz, 1H), 7.18 (dd, J=8.1, 1.7 Hz, 1H), 7.27 (td, J=2.2, 1.0 Hz, 1H), 7.36 (s, 1H), 7.48-7.51 (m, 1H), 7.55 (d, J=8.1 Hz, 1H); MS (DCI/NH₃) m/z=340 (M+H)⁺. Anal. calcd. for C₁₉H₂₁N₃OS.1.12 CF₃CO₂H: C, 54.61; H, 4.77; N, 8.99. Found C, 54.54; H, 4.65; N, 8.86.

Example 5

5-(1H-Indol-4-yl)-2-[(endo)-8-methyl-8-azabicyclo[3.2.1]octan-3-yloxy]thiazole trifluoroacetate The product of Example 1A (150 mg, 0.497 mmol) was coupled with 4-indolyl boronic acid (Frontier, 160 mg, 1.0 mmol) according to the procedure outlined in Example 4 to give the title compound as a white solid. ¹H NMR (300 MHz, CD₃OD) δ ppm 2.31-2.58 (m, 8H), 2.85 (s, 3H), 3.90-3.98 (m, 2H), 5.28 (t, J=4.2 Hz, 1H), 6.71 (dd, J=3.2, 0.8 Hz, 1H), 7.13 (d, J=2.7 Hz, 1H), 7.14 (t, J=3.4 Hz, 1H), 7.34 (d, J=3.4 Hz, 1H), 7.39 (ddd, J=6.0, 3.1, 1.0 Hz, 1H), 7.48 (s, 1H); MS (DCI/NH₃) m/z=340 (M+H)⁺. Anal. calcd. for C₁₉H₂₁N₃OS.CF₃CO₂H.0.35H₂O: C, 54.86; H, 4.98; N, 9.14. Found C, 55.21; H, 4.97; N, 8.75.

Example 6

5-(Benzofuran-5-yl)-2-[(endo)-8-methyl-8-azabicyclo[3.2.1]octan-3-yloxy]thiazole trifluoroacetate The product of Example 1A (150 mg, 0.497 mmol) was coupled with benzofuran-5-boronic acid (Maybridge, 240 mg, 1.5 mmol) according to the procedure outlined in Example 4. The title compound was obtained as a white solid. ¹H NMR (300 MHz, CD₃OD) δ ppm 2.30-2.55 (m, 8H), 2.85 (s, 3H), 3.90-3.98 (m, 2H), 5.26 (t, J=4.3 Hz, 1H), 6.87 (dd, J=2.2, 0.8 Hz, 1H), 7.41 (s, 1H), 7.46 (dd, J=8.5, 1.7 Hz, 1H), 7.53 (d, J=8.8 Hz, 1H), 7.75 (d, J=1.7 Hz, 1H), 7.79 (d, J=2.4 Hz, 1H); MS (DCI/NH₃) m/z=341 (M+H)⁺. Anal. calcd. for C₁₉H₂₀N₂O₂S.1.10 CF₃CO₂H: C, 54.66; H, 4.57; N, 6.01. Found C, 54.95; H, 4.53; N, 6.01.

Example 7

5-(Benzo[b]thiophen-5-yl)-2-[(endo)-8-methyl-8-azabicyclo[3.2.1]octan-3-yloxy]thiazole fumarate The product of Example 1A (150 mg, 0.497 mmol) was coupled with 2-(benzo[b]thiophen-5-yl)-4,4,5,5-tetramethyl-1,3,2-dioxaborolane (Maybridge, 260 mg, 1.0 mmol) according to the procedure outlined in Example 4. The mixture was purified by preparative HPLC (Gilson, Xterra® column, 7 µm, 40×100 mm, eluting solvent, MeCN/H₂O (with 0.1 M NH₄HCO₃/NH₄OH, PH=10) (v. 90/10 to 10/90 over 25 minutes), flow rate, 40 mL/min., uv, 254 nm) to provide the free base of the titled compound. The free base was then treated with fumaric acid in EtOAc/EtOH (v, 10:1, 5 mL) at ambient temperature for 16 hours to give the title compound. ¹H NMR (300 MHz, CD₃OD) δ ppm 2.29-2.55 (m, 8H), 2.84 (s, 3H), 3.88-3.95 (m, 2H), 5.26 (t, J=4.30 Hz, 1H), 6.69 (s, 2H), 7.39 (d, J=5.4 Hz, 1H), 7.49-7.55 (m, 2H), 7.63 (d, J=5.8 Hz, 1H), 7.92 (d, J=8.5 Hz, 1H), 7.97 (d, J=1.7 Hz, 1H); MS (DCI/NH₃) m/z=357 (M+H)⁺; Anal. calcd. for C₁₉H₂₀N₂OS₂.1.10C₄H₄O₄: C, 58.05; H, 5.08; N, 5.79. Found C, 58.07; H, 4.98; N, 5.73.

Example 8

5-(2-(trifluoromethyl)-1H-indol-5-yl)-2-[(endo)-8-methyl-8-azabicyclo[3.2.1]octan-3-yloxy])thiazole hemifumarate The product of Example 1A (150 mg, 0.497 mmol) was coupled with 5-(4,4,5,5-tetramethyl-1,3,2-dioxaborolan-2-yl)-2-(trifluoromethyl)-1H-indole (Ref. US 2005043347, 300 mg, 0.965 mmol) according to the procedure outlined in Example 7 to give the title compound as a white solid. ¹H NMR (300 MHz, CD₃OD) δ ppm 2.26-2.53 (m, 8H), 2.76 (s, 3H), 3.75-3.83 (m, 2H), 5.21 (t, J=4.1 Hz, 1H), 6.68 (s, 1H), 6.91 (d, J=1.4 Hz, 1H), 7.38 (s, 1H), 7.47 (s, 1H), 7.48 (s, 1H), 7.77 (s, 1H); MS (DCI/NH₃) m/z=408 (M+H)⁺. Anal. calcd. for C₂₀H₂₀F₃N₃OS.0.90C₄H₄O₄: C, 55.37; H, 4.65; N, 8.21. Found C, 55.47; H, 4.69; N, 8.32.

Example 9

5-(dibenzo[b,d]thiophen-2-yl)-2-[(endo)-8-methyl-8-azabicyclo[3.2.1]octan-3-yloxy]thiazole fumarate The product of Example 1A (150 mg, 0.497 mmol) and dibenzo[b,d]thiophene-2-boronic acid (Acros, 137 mg, 0.60 mmol) were processed according to the procedure outlined in Example 7 to give the title compound as a white solid. $^1$H NMR (300 MHz, CD$_3$OD) δ ppm 2.30-2.57 (m, 8H), 2.84 (s, 3H), 3.90-3.96 (m, 2H), 5.28 (t, J=4.1 Hz, 1H), 6.69 (s, 1H) 7.47-7.54 (m, 2H), 7.61 (s, 1H), 7.64 (dd, J=8.5, 1.7 Hz, 1H), 7.87-7.94 (m, 2H), 8.28-8.35 (m, 1H), 8.37 (d, J=1.7 Hz, 1H); MS (DCI/NH$_3$) m/z=407 (M+H)$^+$. Anal. calcd. for C$_{23}$H$_{22}$N$_2$OS$_2$.1.40C$_4$H$_4$O$_4$: C, 60.36; H, 4.89; N, 4.92. Found C, 60.23; H, 4.94; N, 4.59.

Example 10

2-[(exo)-8-Methyl-8-azabicyclo[3.2.1]octan-3-yloxy]-5-(1H-indol-5-yl)-thiazole tri(hydrochloric acid

Example 10A (exo)-8-Methyl-8-aza-bicyclo[3.2.1]oct-3-yl-4-nitrobenzoate

To a solution of (endo)-tropine (2.82 g, 20.0 mmol), 4-nitrobenzoic acid (3.34 g, 20.0 mmol) and triphenylphosphine (5.24 g, 20.0 mmol) in dry THF (100 mL) was added to diisopropyl azodicarboxylate (4.04 g, 20.0 mmol) at room temperature. The resulting mixture was stirred at ambient temperature for 40 hours, then concentrated under reduced pressure. The residue was purified by chromatography (140 g SiO$_2$, EtOAc:MeOH:NH$_3$.H$_2$O, 90:10:1, Rf=0.30) to provide the titled compound. $^1$H NMR (300 MHz, CD$_3$OD) δ 1.74-2.23 (m, 8H), 2.38 (s, 3H), 3.32-3.38 (m, 2H), 5.23-5.38 (m, 1H), 8.21 (d, J=8.82 Hz, 2H), 8.32 (d, J=8.82 Hz, 2H) ppm; MS (DCI/NH$_3$): 291 (M+H)$^+$.

Example 10B (exo)-8-methyl-8-aza-bicyclo[3.2.1]octan-3-ol

The product of Example 10A (5.0 g, 0.017 mol) in ethanol (10 mL) was treated with NaOH (1 N, 200 mL) at room temperature for 40 hours. The mixture was extracted with CHCl$_3$/PrOH (v. 90/10, 3×100 mL). The combined extracts were concentrated under reduced pressure to provide the title compound. $^1$H NMR (300 MHz, CD$_3$OD) δ 1.55-1.69 (m, 4H), 1.80 (m, 2H), 1.99-2.09 (m, 2H), 2.28 (s, 3H), 3.14-3.21 (m, 2H), 3.79-3.93 (m, 1H) ppm. MS (DCI/NH$_3$): 142 (M+H)$^+$.

Example 10C

5-Bromo-2-[(exo)-8-methyl-8-azabicyclo[3.2.1]octan-3-yloxy]thiazole

The product of Example 10B (420 mg, 3.0 mmol) was coupled with 2,5-dibromothiazole (Aldrich, 969 mg, 4.0 mmol) according to the procedure outlined in Example 1A. The title compound was purified with chromatography (SiO$_2$, CH$_2$Cl$_2$/MeOH/NH$_3$.H$_2$O, v. 90/10/2, R$_f$=0.40) to give the title compound. $^1$H NMR (300 MHz, CD$_3$OD) δ ppm 1.82-2.12 (m, 4H), 2.19-2.33 (m, 2H), 2.33-2.46 (m, 2H), 2.64 (s, 3H), 3.57-3.83 (m, 2H), 5.15-5.51 (m, 1H), 7.12 (s, 1H); MS (DCI/NH$_3$) m/z 303 (M+1)$^+$. 305 (M+1)$^+$.

Example 10D

2-[(exo)-8-Methyl-8-azabicyclo[3.2.1]octan-3-yloxy]-5-(1H-indol-5-yl)-thiazole

The product of Example 10C (200 mg, 0.66 mmol) was coupled with 5-indolyl boronic acid (Frontier, 160 mg, 1.0 mmol) according to the procedure of Example 1B. The title compound was purified by chromatography (SiO$_2$, CH$_2$Cl$_2$/MeOH/NH$_3$.H$_2$O, v. 90/10/2, R$_f$=0.10). $^1$H NMR (300 MHz, CD$_3$OD) δ ppm 1.89-2.11 (m, 4H), 2.21-2.32 (m, 2H), 2.34-2.46 (m, 2H), 2.60 (s, 3H), 3.58-3.85 (m, 2H), 5.14-5.41 (m, 1H), 6.45 (d, J=4.07 Hz, 1H), 7.22-7.30 (m, 3H), 7.39 (d, J=8.48 Hz, 1H), 7.64 (s, 1H); MS (DCI/NH$_3$) m/z 340 (M+1)$^+$.

Example 10E

2-[(exo)-8-Methyl-8-azabicyclo[3.2.1]octan-3-yloxy]-5-(1H-indol-5-yl)-thiazole tri(hydrochloric acid The product of Example 10D (210 mg, 0.62 mmol) was treated with HCl (Aldrich, 4 M in dioxane, 0.5 mL, 2.0 mmol) in EtOAc (5 mL) at ambient temperature for 10 hours to give the title compound as a white solid. $^1$H NMR (300 MHz, Pyridine-D$_5$) δ ppm 1.84-1.94 (m, 2H), 2.16-2.29 (m, 2H), 2.40-2.51 (m, J=3.07 Hz, 2H), 2.80 (s, 3H), 2.90-3.14 (m, 2H), 3.87-4.00 (m, 2H), 5.40-5.56 (m, 1H), 6.75 (s, 1H), 7.45-7.53 (m, 2H), 7.59-7.66 (m, 2H), 8.01 (s, 1H), 12.28 (s, 1H); MS (DCI/NH$_3$) m/z 340 (M+1)$^+$. Anal. calcd. for C$_{14}$H$_{18}$ClN$_3$.3.52HCl.0.10EtOAc: C, 48.89; H, 5.35; N, 8.82. Found: C, 49.22; H, 4.86; N, 8.42.

Example 11

2-[(exo)-8-Methyl-8-azabicyclo[3.2.1]octan-3-yloxy]-5-(1H-indol-6-yl)-thiazole tri(hydrochloric acid

Example 11A

2-[(exo)-8-Methyl-8-azabicyclo[3.2.1]octan-3-yloxy]-5-(1H-indol-5-yl)-thiazole

The product of Example 10C (200 mg, 0.66 mmol) was coupled with 6-indolyl boronic acid (Frontier, 160 mg, 1.0 mmol) according to the procedure outlined in Example 1B. The title compound was purified by chromatography (SiO$_2$, CH$_2$Cl$_2$/MeOH/NH$_3$.H$_2$O, v. 90/10/2, R$_f$=0.10). $^1$H NMR (300 MHz, CDCl$_3$) δ ppm 1.95-2.30 (m, 3H), 2.31-2.56 (m, 5H), 2.74 (s, 3H), 3.62-3.90 (m, 2H), 5.24-5.56 (m, 1H), 6.51-6.63 (m, 1H), 7.20-7.25 (m, 2H), 7.44 (s, 1H), 7.62 (d, J=8.14 Hz, 1H), 8.22 (s, 1H); MS (DCI/NH$_3$) m/z 340 (M+1)$^+$.

Example 11B

2-[(exo)-8-Methyl-8-azabicyclo[3.2.1]octan-3-yloxy]-5-(1H-indol-5-yl)-thiazole tri(hydrochloric acid The product of Example 11A (140 mg, 0.41 mmol) was treated with HCl (Aldrich, 4 M in dioxane, 0.5 mL, 2.0 mmol) in EtOAc (5 mL) at ambient temperature for 10 hours to give the title compound as a white solid. $^1$H NMR (300 MHz, Pyridine-D$_5$) δ ppm 1.83-1.94 (m, 2H), 2.17-2.33 (m, 2H), 2.37-2.55 (m, 2H), 2.85 (s, 3H), 2.93-3.19 (m, 2H), 3.91-4.03 (m, 2H), 5.33-5.61 (m, 1H), 6.71-6.75 (m, 1H), 7.44 (dd, J=8.00, 1.60 Hz, 1H) 7.56-7.59 (m, 1H), 7.60 (s, 1H), 7.75-7.86 (m, 2H), 12.23 (s, 1H); MS (DCI/NH$_3$) m/z 340 (M+1)$^+$. Anal. calcd. for C$_{14}$H$_{18}$ClN$_3$.3.70HCl.1.30H$_2$O: C, 45.84; H, 5.53; N, 8.44. Found: C, 45.80; H, 5.13; N, 8.06.

Example 12

2-[(exo)-8-Methyl-8-azabicyclo[3.2.1]octan-3-yloxy]-5-phenyl-thiazole hydrochloric acid

Example 12A

2-[(exo)-8-Methyl-8-azabicyclo[3.2.1]octan-3-yloxy]-5-phenyl-thiazole

The product of Example 10C (100 mg, 0.33 mmol) was coupled with phenyl boronic acid (Aldrich, 61 mg, 1.0 mmol) according to the procedure outlined in Example 1B. The title compound was purified by chromatography (SiO$_2$, CH$_2$Cl$_2$/MeOH/NH$_3$.H$_2$O, v. 90/10/2, R$_f$=0.40). $^1$H NMR (300 MHz, CDCl$_3$) δ ppm 2.01-2.23 (m, 2H), 2.28-2.50 (m, 4H), 2.48-2.71 (m, 2H), 2.76 (s, 3H), 3.63-3.98 (m, 2H), 5.09-5.64 (m, 1H), 7.27-7.55 (m, 6H); MS (DCI/NH$_3$) m/z 301 (M+1)$^+$.

Example 12B

2-[(exo)-8-Methyl-8-azabicyclo[3.2.1]octan-3-yloxy]-5-phenyl-thiazole hydrochloric acid The product of Example 12A (90 mg, 0.30 mmol) was treated with HCl (Aldrich, 4 M in dioxane, 0.25 mL, 1.0 mmol) in EtOAc (5 mL) at ambient temperature for 10 hours to give the title compound as a white solid. $^1$H NMR (300 MHz, Pyridine-D$_5$) δ ppm 1.91-2.34 (m, 4H), 2.34-2.49 (m, 2H), 2.53-2.67 (m, 2H), 2.83 (s, 3H), 3.91-4.19 (m, 2H), 5.29-5.61 (m, 1H), 7.17-7.63 (m, 6H); MS (DCI/NH$_3$) m/z 301 (M+1)$^+$.

Example 13

2-[(exo)-8-Methyl-8-azabicyclo[3.2.1]octan-3-yloxy]-5-(pyridin-3-yl)-thiazole tri(hydrochloric acid)

Example 13A

The product of Example 10C (100 mg, 0.33 mmol) was coupled with 3-pyridinyl boronic acid (Aldrich, 62 mg, 1.0 mmol) according to the procedure outlined in Example 1B. The title compound was purified with chromatography (SiO$_2$, CH$_2$Cl$_2$/MeOH/NH$_3$.H$_2$O, v. 90/10/2, R$_f$=0.40). $^1$H NMR (300 MHz, CDCl$_3$) δ ppm 1.88-2.05 (m, 2H), 2.19-2.51 (m, 6H), 2.64 (s, 3H), 3.56-3.76 (m, 2H), 5.19-5.46 (m, 1H), 7.28 (ddd, J=7.80, 3.00, 0.60 Hz, 1H), 7.32 (s, 1H), 7.66-7.74 (m, 1H), 8.52 (dd, J=4.92, 1.53 Hz, 1H), 8.71 (d, J=1.70 Hz, 1H); MS (DCI/NH$_3$) m/z 302 (M+1)$^+$.

Example 13B

2-[(exo)-8-Methyl-8-azabicyclo[3.2.1]octan-3-yloxy]-5-(pyridin-3-yl)-thiazole tri(hydrochloric acid)

The product of Example 13A (100 mg, 0.33 mmol) was treated with HCl (Aldrich, 4 M in dioxane, 0.25 mL, 1.0 mmol) in EtOAc (5 mL) at ambient temperature for 10 hours to give the title compound as a white solid. $^1$H NMR (300 MHz, CD$_3$OD) δ ppm 2.05-2.31 (m, 4H), 2.33-2.49 (m, 2H), 2.54-2.69 (m, 2H), 2.84 (s, 3H), 3.95-4.15 (m, 2H), 5.33-5.73 (m, 1H), 7.90 (s, 1H), 8.10 (dd, J=8.14, 5.76 Hz, 1H), 8.62-8.83 (m, 2H), 9.12 (d, J=2.03 Hz, 1H); MS (DCI/NH$_3$) m/z 301 (M+1)$^+$. Anal. Calculated for C$_{16}$H$_{19}$N$_3$OS.3.78 HCl.1.78H$_2$O: C, 40.68; H, 5.63; N, 8.90. Found: C, 40.34; H, 5.24; N, 8.70.

Example 14

2-[(endo)-8-Methyl-8-azabicyclo[3.2.1]octan-3-yloxy]-5-phenyl-1,3,4-thiadiazole

Example 14A

2-Bromo-5-phenyl-1,3,4-thiadiazole

A stirred solution of 2-amino-5-phenyl-[1,3,4]thiadiazole (Aldrich, 0.885 g, 5.0 mmol) in MeCN (anhydrous, Aldrich, 20 mL) was treated with copper (II) bromide (Acros, 2.23 g, 10.0 mmol) and iso-amyl nitrite (Aldrich, 1.17 g, 10.0 mmol) at ambient temperature for 10 hours. The mixture was quenched with saturated ammonium chloride (5 mL) and extracted with ether (3×40 mL). The combined extracts were concentrated and purified by flash chromatography [EtOAc/hexanes=20/80 (v.), R$_f$=0.6] to afford the title compound. $^1$H NMR (300 MHz, CDCl$_3$) δ ppm 7.44-7.55 (m, 3H), 7.85-7.94 (m, 2H). MS (DCI/NH$_3$) m/e 241 (M+H)$^+$, 243 (M+H)$^+$.

Example 14B

2-[(endo)-8-methyl-8-azabicyclo[3.2.1]octan-3-yloxy]-5-phenyl-1,3,4-thiadiazole A solution of tropine (Aldrich, 140 mg, 1.0 mmol) in THF (anhydrous, Aldrich, 10 mL) was stirred with potassium tert-butoxide (Aldrich, 114 mg, 1.0 mmol) at ambient temperature for 1.0 hour. The product of Example 14A (241 mg, 1.0 mmol) was then added at 10-20° C., and the mixture was stirred at 60° C. for 10 hours and then quenched with water (1 mL) and concentrated. The residue was diluted with CHCl$_3$ (30 mL) and washed with brine (2×5 mL). The organic solution was concentrated and the residue was purified using chromatography (SiO$_2$, CH$_2$Cl$_2$/MeOH/NH$_3$.H$_2$O, v. 90/10/2, R$_f$=0.15) to give the title compound. $^1$H NMR (300 MHz, CD$_3$OD) δ ppm 2.31-2.44 (m, 4H), 2.46-2.59 (m, 4H), 2.84 (s, 3H), 3.78-4.11 (m, 2H), 5.36 (t, J=3.05 Hz, 1H), 7.43-7.61 (m, 3H), 7.77-7.93 (m, 2H); MS (DCI/NH$_3$) m/z 302 (M+1)$^+$.

Example 15

2-(1H-indol-5-yl)-5-[(endo)-8-methyl-8-azabicyclo[3.2.1]octan-3-yloxy]-1,3,4-thiadiazole bis O-toluenesulfonic acid)

Example 15A

2,5-Dibromo-1,3,4-thiadiazole

To a stirred solution of 2,5-diamino-[1,3,4]thiadiazole (Aldrich, 13.0 g, 72.2 mmol) in MeCN (anhydrous, Aldrich, 250 mL) was added copper (II) bromide (Acros, 18.80 g, 83.7 mmol) and iso-amyl nitrite (Aldrich, 17.0 g, 145.0 mmol) at 0-10° C. The mixture was then stirred at ambient temperature for 10 hours. The mixture was quenched with saturated ammonium chloride (100 mL) and extracted with ether (3×200 mL). The combined extracts were concentrated and purified by flash chromatography [EtOAc/hexanes=20/80 (v.), R$_f$=0.6] to afford the title compound. MS (DCI/NH$_3$) m/e 243 (M+H)$^+$, 245 (M+H)$^+$, 247 (M+H)$^+$.

Example 15B

2-Bromo-5-[(endo)-8-methyl-8-azabicyclo[3.2.1]octan-3-yloxy]-1,3,4-thiadiazole

The product of Example 15A (2.44 g, 10 mmol) was coupled with tropine (Aldrich, 1.40 g, 10.0 mmol) according to the procedure outlined in Example 14A. The title compound was purified by chromatography (SiO$_2$, CH$_2$Cl$_2$/MeOH/NH$_3$.H$_2$O, v. 90/10/2, R$_f$=0.10). $^1$H NMR (300 MHz, CDCl$_3$) δ ppm 1.83-1.96 (m, 2H), 1.98-2.12 (m, 4H), 2.15-2.28 (m, 2H), 2.30 (s, 3H), 3.08-3.30 (m, 2H), 5.27 (t, J=5.09 Hz, 1H); MS (DCI/NH$_3$) m/z 304 (M+1)$^+$. 306 (M+1)$^+$.

Example 15C 2-(1H-Indol-5-yl)-5-[(endo)-8-methyl-8-azabicyclo[3.2.1]octan-3-yloxy]-1,3,4-thiadiazole The product of Example 15B (150 mg, 0.49 mmol) was coupled with 5-indolyl boronic acid (Frontier, 160 mg, 1.0 mmol) were processed according to the procedure outlined in Example 1B. The title compound was purified by chromatography (SiO$_2$, CH$_2$Cl$_2$/MeOH/NH$_3$.H$_2$O, v. 90/10/2, R$_f$=0.10). $^1$H NMR (300 MHz, CD$_3$OD) δ ppm 1.97-2.27 (m, 8H), 2.34 (s, 3H), 3.17-3.26 (m, 2H), 5.18 (t, J=4.92 Hz, 1H), 6.55 (d, J=2.37 Hz, 1H), 7.33 (d, J=3.39 Hz, 1H), 7.47 (d, J=8.48 Hz, 1H), 7.62 (dd, J=8.65, 1.87 Hz, 1H), 8.02 (s, 1H); MS (DCI/NH$_3$) m/z 341 (M+1)$^+$.

Example 15D 2-(1H-Indol-5-yl)-5-[(endo)-8-methyl-8-azabicyclo[3.2.1]octan-3-yloxy]-1,3,4-thiadiazole bis(p-toluenesulfonic acid)

The product of Example 15C (100 mg, 0.29 mmol) was treated with p-TsOH.H$_2$O (57, mg, 0.3 mmol) in EtOAc (5 mL) at ambient temperature for 10 hours to give the title compound as a white solid. $^1$H NMR (300 MHz, CD$_3$OD) δ ppm 2.32-2.58 (m, 14H) 2.85 (s, 3H), 3.85-4.10 (m, 2H), 5.33 (t, J=4.07 Hz, 1H), 6.56 (d, J=3.39 Hz, 1H), 7.23 (d, J=8.14 Hz, 4H), 7.34 (d, J=3.05 Hz, 1H), 7.47-7.51 (m, 1H), 7.63 (dd, J=8.65, 1.53 Hz, 1H), 8.04 (d, J=1.36 Hz, 1H); MS (DCI/NH$_3$) m/z 341 (M+1)$^+$. Anal. calcd. for C$_{18}$H$_{20}$N$_4$OS.1.90TsOH.1.50H$_2$O: C, 54.12; H, 5.54; N, 8.07. Found: C, 53.83; H, 5.25; N, 8.38.

Example 16

2-(Benzofuran-5-yl)-5-[(endo)-8-methyl-8-azabicyclo[3.2.1]octan-3-yloxy)-1,3,4-thiadiazole fumarate The product of Example 15B (150 mg, 0.495 mmol) was coupled with benzofuran-5-boronic acid (Maybridge, 240 mg, 1.5 mmol) according to the procedure outlined in Example 7 to give the title compound as a white solid. $^1$H NMR (300 MHz, CD$_3$OD) δ ppm 2.28-2.58 (m, 8H), 2.79 (s, 3H), 3.80-3.88 (m, 2H), 5.35 (t, J=4.1 Hz, 1H), 6.68 (s, 2H), 6.96 (dd, J=2.4, 1.0 Hz, 1H), 7.63 (d, J=8.5 Hz, 1H), 7.83 (dd, J=8.6, 1.9 Hz, 1H), 7.87 (d, J=2.4 Hz, 1H), 8.12 (d, J=1.7 Hz, 1H); MS (DCI/NH$_3$) m/z 342 (M+H)$^+$. Anal. calcd. for C$_{18}$H$_{19}$N$_3$O$_2$S.1.00C$_4$H$_4$O$_4$: C, 57.76; H, 5.07; N, 9.18. Found C, 57.56; H, 4.97; N, 9.45.

Example 17

2-(Benzo[b]thiophen-5-yl)-5-[(e n do)-8-methyl-8-azabicyclo[3.2.1]octan-3-yloxy]-1,3,4-thiadiazole fumarate The product of Example 15B (303 mg, 1.0 mmol) was coupled with 2-(benzo[b]thiophen-5-yl)-4,4,5,5-tetramethyl-1,3,2-dioxaborolane (Maybridge, 520 mg, 2.0 mmol) according to the procedure outlined in Example 7 to give the title compound as a white solid. $^1$H NMR (300 MHz, CD$_3$OD) δ ppm 2.33-2.45 (m, 4H), 2.49-2.58 (m, 4H), 2.83 (s, 3H) 3.90-3.97 (m, 2H), 5.37 (t, J=4.20 Hz, 1H), 6.69 (s, 2H), 7.49 (dd, J=5.4, 0.7 Hz, 1H), 7.72 (d, J=5.4 Hz, 1H), 7.85 (dd, J=8.5, 2.4 Hz, 1H), 8.05 (d, J=8.5 Hz, 1H), 8.32 (d, J=1.0 Hz, 1H); MS (DCI/NH$_3$) m/e=358 (M+H)$^+$. Anal. calcd. for C$_{18}$H$_{19}$N$_3$OS$_2$.1.1C$_4$H$_4$O$_4$: C, 55.45; H, 4.86; N, 8.66. Found C, 55.27; H, 4.89; N, 8.54.

Example 18

2-(3-Fluorophenyl)-5-[(endo)-8-methyl-8-azabicyclo[3.2.1]octan-3-yloxy]-1,3,4-thiadiazole fumarate The product of Example 15B (150 mg, 0.495 mmol) was coupled with 3-fluorophenylboronic acid (Aldrich, 168 mg, 1.2 mmol) according to the procedure outlined in Example 7 to give the title compound. $^1$H NMR (300 MHz, CD$_3$OD) δ ppm 2.32-2.42 (m, 4H), 2.48-2.56 (m, 4H), 2.83 (s, 3H), 3.90-3.95 (m, 2H), 5.36 (t, J=4.2 Hz, 1H), 6.69 (s, 2H), 7.24-7.32 (m, 1H), 7.53 (td, J=8.2, 5.6 Hz, 1H), 7.62-7.68 (m, 2H); MS (DCI/NH$_3$) m/z=320 (M+H)$^+$. Anal. calcd. for C$_{16}$H$_{18}$FN$_3$OS.1.15C$_4$H$_4$O$_4$: C, 54.63; H, 5.03; N, 9.28. Found C, 54.50; H, 5.29; N, 9.20.

Example 19

2-[(endo)-8-methyl-8-azabicyclo[3.2.1]octan-3-yloxy]-5-m-tolyl-1,3,4-thiadiazole fumarate The product of Example 15B (150 mg, 0.495 mmol) was coupled with m-tolylboronic acid (Aldrich, 180 mg, 1.32 mmol) according to the procedure outlined in Example 7 to give the title compound as a white solid. $^1$H NMR (300 MHz, CD$_3$OD) δ ppm 2.29-2.44 (m, 8H), 2.52 (s, 3H), 2.83 (s, 3H), 3.85-2.96 (m, 2H), 5.35 (t, J=4.1 Hz, 1H), 6.69 (s, 2H), 7.30-7.43 (m, 2H), 7.59-7.76 (m, 2H); MS (DCI/NH$_3$) m/z=316 (M+H)$^+$; Anal. calcd. for C$_{17}$H$_{21}$N$_3$OS.1.05C$_4$H$_4$O$_4$: C, 58.23; H, 5.81; N, 9.61. Found C, 58.16; H, 5.85; N, 9.57.

Example 20

2-(4-Fluorophenyl)-5-[(endo)-8-methyl-8-azabicyclo[3.2.1]octan-3-yloxy]-1,3,4-thiadiazole fumarate The product of Example 15B (150 mg, 0.495 mmol) was coupled with 4-fluorophenylboronic acid (Aldrich, 130 mg, 0.93 mmol) according to the procedure outlined in Example 7 to give the title compound as a white solid. $^1$H NMR (300 MHz, CD$_3$OD) δ ppm 2.31-2.42 (m, 4H), 2.49-2.55 (m, 4H), 2.83 (s, 3H), 3.88-3.95 (m, 2H), 5.34 (t, J=4.2 Hz, 1H), 6.69 (s, 2H), 7.21-7.30 (m, 2H), 7.85-7.93 (m, 2H); MS (DCI/NH$_3$) m/z=320 (M+H)$^+$. Anal. calcd. for $C_{16}H_{18}FN_3OS.1.10C_4H_4O_4$: C, 54.81; H, 5.05; N, 9.40. Found C, 54.82; H, 4.85; N, 9.52.

Example 21

2-(3-Chlorophenyl)-5-[(endo)-8-methyl-8-azabicyclo[3.2.1]octan-3-yloxy]-1,3,4-thiadiazole fumarate The product of Example 15B (150 mg, 0.495 mmol) was coupled with 3-chlorophenylboronic acid (Aldrich, 187 mg, 1.2 mmol) were processed according to the procedure outlined in Example 7 to give the title compound as a white solid. $^1$H NMR (300 MHz, CD$_3$OD) δ ppm 2.33-2.40 (m, 4H), 2.48-2.55 (m, 4H), 2.84 (s, 3H), 3.88-3.96 (m, 2H), 5.38 (t, J=4.2 Hz, 1H), 6.69 (s, 2H), 7.46-7.57 (m, 2H), 7.76 (dt, J=7.1, 1.7 Hz, 1H), 7.89-7.92 (m, 1H); MS (DCI/NH$_3$) m/z=336 (M+H)$^+$; Anal. calcd. for $C_{16}H_{18}ClN_3OS.0.30C_4H_4O_4$: C, 52.31; H, 4.80; N, 8.63. Found C, 52.18; H, 4.85; N, 8.73.

Example 22

2-(1H-Indol-6-yl)-5-[(endo)-8-methyl-8-azabicyclo[3.2.1]octan-3-yloxy]-1,3,4-thiadiazole p-toluenesulfonic acid

Example 22A

2-(1H-Indol-6-yl)-5-[(endo)-8-methyl-8-azabicyclo[3.2.1]octan-3-yloxy]-1,3,4-thiadiazole The product of Example 15B (150 mg, 0.49 mmol) was coupled with 6-indolyl boronic acid (Frontier, 160 mg, 1.0 mmol) were processed according to the procedure outlined in Example 1B. The title compound was purified by chromatography (SiO$_2$, CH$_2$Cl$_2$/MeOH/NH$_3$.H$_2$O, v. 90/10/2, R$_f$=0.10). $^1$H NMR (300 MHz, CD$_3$OD) δ ppm 2.08-2.42 (m, 8H), 2.50 (s, 3H), 3.39-3.52 (m, 2H), 5.23 (t, J=4.58 Hz, 1H), 6.52 (d, J=3.05 Hz, 1H), 7.39 (d, J=3.39 Hz, 1H), 7.47 (dd, J=8.20, 1.50 Hz 1H) 7.62-7.66 (m, 1H) 7.90 (s, 1H) 8.54 (s, 1H); MS (DCI/NH$_3$) m/z 341 (M+1)$^+$.

Example 22B

2-(1H-Indol-6-yl)-5-[(endo)-8-methyl-8-azabicyclo[3.2.1]octan-3-yloxy]-1,3,4-thiadiazole p-toluenesulfonic acid The product of Example 22A (130 mg, 0.38 mmol) was treated with p-TsOH.H$_2$O (144, mg, 0.76 mmol) in EtOAc (10 mL) at ambient temperature for 10 hours to give the title compound as a white solid. $^1$H NMR (300 MHz, CD$_3$OD) δ ppm 2.18-2.70 (m, 11H), 2.85 (s, 3H) 3.88-4.03 (m, 2H), 5.35 (t, J=4.41 Hz, 1H), 6.53 (d, J=3.05 Hz, 1H), 7.23 (d, J=7.80 Hz, 2H), 7.40 (d, J=8.31, 1.53 Hz, 1H), 7.65 (d, J=8.48 Hz, 1H), 7.71 (d, J=8.14 Hz, 2H), 7.91 (s, 1H); MS (DCI/NH$_3$) m/z 341 (M+1)$^+$. Anal. calcd. for $C_{18}H_{20}N_4OS.1.10TsOH.0.20H_2O$: C, 57.86; H, 5.52; N, 10.50. Found: C, 57.90; H, 5.18; N, 10.19.

Example 23

2-(1H-Indol-4-yl)-5-[(endo)-8-methyl-8-azabicyclo[3.2.1]octan-3-yloxy]-1,3,4-thiadiazole p-toluenesulfonic acid

Example 23A

2-(1H-Indol-4-yl)-5-[(endo)-8-methyl-8-azabicyclo[3.2.1]octan-3-yloxy]-1,3,4-thiadiazole The product of Example 15B (150 mg, 0.49 mmol) was coupled with 6-indolyl boronic acid (Frontier, 160 mg, 1.0 mmol) according to the procedure outlined in Example 1B. The title compound was purified with chromatography (SiO$_2$, CH$_2$Cl$_2$/MeOH/NH$_3$.H$_2$O, v. 90/10/2, R$_f$=0.10). $^1$H NMR (300 MHz, CD$_3$OD) δ ppm 1.98-2.32 (m, 8H), 2.34 (s, 3H), 3.17-3.27 (m, 2H), 5.22 (t, J=4.92 Hz, 1H), 7.05 (d, J=2.37 Hz, 1H), 7.20 (t, J=7.60 Hz, 1H), 7.41 (d, J=3.39 Hz, 1H), 7.48 (d, J=7.46 Hz, 1H), 7.56 (d, J=8.14 Hz, 1H); MS (DCI/NH$_3$) m/z 341 (M+1)$^+$.

Example 23B

2-(1H-Indol-4-yl)-5-[(endo)-8-methyl-8-azabicyclo[3.2.1]octan-3-yloxy]-1,3,4-thiadiazole p-toluenesulfonic acid The product of Example 22A (150 mg, 0.44 mmol) was treated with p-TsOH.H$_2$O (168, mg, 0.88 mmol) in EtOAc (10 mL) at ambient temperature for 10 hours to give the title compound as a white solid. $^1$H NMR (300 MHz, CD$_3$OD) δ ppm 2.36-2.63 (m, 11H), 2.85 (s, 3H), 3.84-4.11 (m, 2H), 5.38 (t, J=4.75 Hz, 1H), 7.05 (d, J=4.07 Hz, 1H), 7.16-7.27 (m, 3H), 7.43 (d, J=3.05 Hz, 1H), 7.49 (d, J=7.46 Hz, 1H), 7.57 (d, J=8.14 Hz, 1H), 7.70 (d, J=8.10 Hz, 2H); MS (DCI/NH$_3$) m/z 341 (M+1)$^+$. Anal. calcd. for $C_{18}H_{20}N_4OS.1.00TsOH.0.40H_2O$: C, 57.76; H, 5.58; N, 10.78. Found: C, 57.33; H, 5.25; N, 10.49.

Example 24

2-(3-Cyanophenyl)-5-[(endo)-8-methyl-8-azabicyclo[3.2.1]octan-3-yloxy]-1,3,4-thiadiazole trifluoroacetate The product of Example 15B (150 mg, 0.495 mmol) was coupled with 3-cyanophenylboronic acid (Aldrich, 185 mg, 1.2 mmol) according to the procedure outlined in Example 4 to give the title compound as a white solid. $^1$H NMR (300 MHz, CD$_3$OD) δ ppm 2.32-2.71 (m, 8H), 2.85 (s, 3H), 3.92-3.99 (m, 2H), 5.40 (t, J=4.4 Hz, 1H), 7.70 (t, J=7.8 Hz, 1H), 7.88 (dt, J=7.8, 1.4 Hz, 1H), 8.16 (ddd, J=8.1, 1.8, 1.0 Hz, 1H), 8.24 (t, J=1.7 Hz, 1H); MS (DCI/NH$_3$) m/z=327 (M+H)$^+$. Anal. calcd. for $C_{17}H_{18}N_4OS.1.40CF_3CO_2H.0.60H_2O$: C, 47.86; H, 4.18; N, 11.28. Found C, 47.63; H, 3.88; N, 11.56.

Example 25

2-(3-Trifluoromethylphenyl)-5-[(endo)-8-methyl-8-azabicyclo[3.2.1]octan-3-yloxy)-1,3,4-thiadiazole fumarate The product of Example 15B (150 mg, 0.495 mmol) was coupled with 3-trifluoromethylphenylboronic acid (Aldrich, 228 mg, 1.2 mmol) according to the procedure outlined in Example 7 to give the title compound as a white solid. $^1$H NMR (300 MHz, CD$_3$OD) δ ppm 2.31-2.57 (m, 8H), 2.85 (s, 3H), 3.92-3.98 (m, 2H), 5.30-5.42 (m, 1H), 6.70 (s, 2.80H), 7.72 (t, J=7.8 Hz, 1H), 7.83 (d, J=7.8 Hz, 1H), 8.09 (d, J=7.8 Hz, 1H), 8.17 (s, 1H); MS (DCI/NH$_3$) m/z=370 (M+H)$^+$. Anal. calcd. for C$_{17}$H$_{18}$F$_3$N$_3$OS.1.40C$_4$H$_4$O$_4$: C, 51.03; H, 4.47; N, 7.90. Found C, 51.17; H, 4.55; N, 7.75.

Example 26

2-(4-Chlorophenyl)-5-((1R,3R,5S)-8-methyl-8-azabicyclo[3.2.1]octan-3-yloxy)-1,3,4-thiadiazole fumarate The product of Example 15B (150 mg, 0.495 mmol) was coupled with 4-chlorophenylboronic acid (Aldrich, 187 mg, 1.2 mmol) according to the method described in Example 7 to give the title compound as a white solid. $^1$H NMR (300 MHz, CD$_3$OD) δ ppm 2.32-2.39 (m, 4H), 2.46-2.55 (m, 4H), 2.84 (s, 3H), 3.85-2.96 (m, 2H), 5.33-5.39 (m, 1H), 6.69 (s, 2H), 7.53 (d, J=8.5 Hz, 2H), 7.85 (d, J=8.5 Hz, 2H); MS (DCI/NH$_3$) m/z=336 (M+H)$^+$. Anal. calcd. for C$_{16}$H$_{18}$ClN$_3$OS.1.15C$_4$H$_4$O$_4$: C, 52.72; H, 4.85; N, 8.95. Found C, 52.76; H, 4.77; N, 9.12.

Example 27

2-(2-(Trifluoromethyl)-1H-indol-5-yl)-5-[(endo)-8-methyl-8-azabicyclo[3.2.1]octan-3-yloxy]-1,3,4-thiadiazole bis(fumarate)

The product of Example 15B (150 mg, 0.495 mmol) was coupled with 5-(4,4,5,5-tetramethyl-1,3,2-dioxaborolan-2-yl)-2-(trifluoromethyl)-1H-indole (Ref. Patent Application Publication No. US 2005043347, 380 mg, 1.22 mmol) according to the procedure outlined in Example 7 to give the title compound as a white solid. $^1$H NMR (300 MHz, CD$_3$OD) δ ppm 2.30-2.64 (m, 8H), 2.86 (s, 3H), 3.93-2.98 (m, 2H), 5.32-5.39 (m, 1H), 6.72 (s, 5H), 7.03 (s, 1H) 7.57 (d, J=8.5 Hz, 1H) 7.83 (dd, J=8.6, 1.9 Hz, 1H) 8.15 (d, J=1.7 Hz, 1H); MS (DCI/NH$_3$) m/z=409 (M+H)$^+$. Elemental Anal. calcd. for C$_{19}$H$_{19}$F$_3$N$_4$OS.2.5C$_4$H$_4$O$_4$.0.7H$_2$O: C, 48.97; H, 4.31; N, 7.88. Found C, 48.99; H, 4.30; N, 7.62.

Example 28

2-(3-Chloro-4-fluorophenyl)-5-[(endo)-8-methyl-8-azabicyclo[3.2.1]octan-3-yloxy]-1,3,4-thiadiazole fumarate The product of Example 15B (150 mg, 0.495 mmol) was coupled with 3-chloro-4-fluorophenylboronic acid (Aldrich, 190 mg, 1.09 mmol) according to the procedure outlined in Example 7 to give the title compound as a white solid. $^1$H NMR (300 MHz, CD$_3$OD) δ ppm 2.32-2.42 (m, 4H) 2.44-2.56 (m, 4H), 2.83 (s, 3H), 3.88-2.96 (m, 2H), 5.32-5.39 (m, 1H), 6.69 (s, 2.2H), 7.41 (t, J=8.6 Hz, 1H), 7.82 (ddd, J=8.7, 4.5, 2.4 Hz, 1H), 8.03 (dd, J=7.0, 2.2 Hz, 1H); MS (DCI/NH$_3$) m/z=354 (M+H)$^+$. Anal. calcd. for C$_{16}$H$_{17}$ClFN$_3$OS.1.10C$_4$H$_4$O$_4$: C, 50.88; H, 4.48; N, 8.73. Found C, 50.93; H, 4.53; N, 8.67.

Example 29

2-(4-(Trifluoromethyl)phenyl)-5-[(endo)-8-methyl-8-azabicyclo[3.2.1]octan-3-yloxy]-1,3,4-thiadiazole fumarate The product of Example 15B (150 mg, 0.495 mmol) was coupled with 4-(trifluoromethyl)phenylboronic acid (Aldrich, 190 mg, 1.0 mmol) according to the procedure outlined in Example 7 to give the title compound as a white solid. $^1$H NMR (300 MHz, CD$_3$OD) δ ppm 2.32-2.43 (m, 4H), 2.50-2.57 (m, 4H), 2.83 (s, 3H) 3.86-3.95 (m, 2H), 5.32-5.43 (m, 1H), 6.69 (s, 2.30H), 7.82 (d, J=8.5 Hz, 2H), 8.06 (d, J=8.1 Hz, 2H), MS (DCI/NH$_3$) m/e=370 (M+H)$^+$. Anal. calcd. for C$_{17}$H$_{18}$F$_3$N$_3$OS.1.15C$_4$H$_4$O$_4$: C, 51.59; H, 4.53; N, 8.36. Found C, 51.38; H, 4.48; N, 8.36.

Example 30

2-(4-Methoxyphenyl)-5-[(endo)-8-methyl-8-azabicyclo[3.2.1]octan-3-yloxy]-1,3,4-thiadiazole fumarate The product of Example 15B (150 mg, 0.495 mmol) was coupled with 4-methoxyphenylboronic acid (Aldrich, 152 mg, 1.0 mmol) according to the procedure outlined in Example 7 to give the title compound as a white solid. $^1$H NMR (300 MHz, CD$_3$OD) δ ppm 2.29-2.42 (m, 4H), 2.44-2.56 (m, 4H), 2.83 (s, 3H), 3.86 (s, 3H), 3.88-3.94 (m, 2H), 5.29-5.36 (m, 1H), 6.69 (s, 2.30H), 7.04 (d, J=8.8 Hz, 2H), 7.78 (d, J=8.8 Hz, 2H); MS (DCI/NH$_3$) m/z=332 (M+H)$^+$. Anal. calcd. for C$_{17}$H$_{21}$N$_3$O$_2$S.1.15C$_4$H$_4$O$_4$: C, 55.80; H, 5.55; N, 9.04. Found C, 55.91; H, 5.34; N, 9.20.

Example 31

2-(3-Aminophenyl)-5-[(endo)-8-methyl-8-azabicyclo[3.2.1]octan-3-yloxy]-1,3,4-thiadiazole hemifumarate The product of Example 15B (152 mg, 0.50 mmol) was coupled with 3-aminophenylboronic acid (Aldrich, 137 mg, 1.0 mmol) according to the procedure outlined in Example 7 to give the title compound as a white solid. $^1$H NMR (300 MHz, CD$_3$OD) δ ppm 2.31-2.38 (m, 4H), 2.45-2.51 (m, 4H), 2.81 (s, 3H), 3.82-3.92 (m, 2H), 5.30-5.38 (m, 1H), 6.68 (s, 1.30H), 6.83 (ddd, J=8.0, 2.2, 1.0 Hz, 1H), 7.05-7.09 (m, 1H), 7.14-7.22 (m, 2H); MS (DCI/NH$_3$) m/z=317 (M+H)$^+$. Anal. calcd. for C$_{16}$H$_{20}$N$_4$OS.0.65C$_4$H$_4$O$_4$: C, 57.01; H, 5.81; N, 14.30. Found C, 56.85; H, 5.88; N, 14.37.

Example 32

2-(4-Ethylphenyl)-5-[(endo)-8-methyl-8-azabicyclo[3.2.1]octan-3-yloxy]-1,3,4-thiadiazole fumarate The product of Example 15B (150 mg, 0.495 mmol) was coupled with 4-ethylphenylboronic acid (Aldrich, 150 mg, 1.0 mmol) according to the procedure outlined in Example 7 to give the fumarate salt as a white solid. $^1$H NMR (300 MHz, CD$_3$OD) δ ppm 1.27 (t, J=7.5 Hz, 5H), 2.31-2.43 (m, 4H), 2.48-2.56 (m, 4H), 2.71 (q, J=7.8 Hz, 2H), 2.83 (s, 3H), 3.87-3.95 (m, 2H), 5.31-5.38 (m, 1H), 6.69 (s, 2.30H), 7.35 (d, J=8.5 Hz, 2H), 7.75 (d, J=8.5 Hz, 2H); MS (DCI/NH$_3$) m/z=330 (M+H)$^+$. Anal. calcd. for C$_{17}$H$_{21}$N$_3$O$_2$S.1.15C$_4$H$_4$O$_4$: C, 58.85; H, 6.04; N, 9.19. Found C, 58.94; H, 6.08; N, 9.34.

Example 33

2-(4-Acetylphenyl)-5-[(endo)-8-methyl-8-azabicyclo[3.2.1]octan-3-yloxy]-1,3,4-thiadiazole trifluoroacetate The product of Example 15B (150 mg, 0.495 mmol) was coupled with 4-acetylphenylboronic acid (Aldrich, 164 mg, 1.0 mmol) according to the procedure outlined in Example 4 to give the title compound as a white solid. $^1$H NMR (300 MHz, CD$_3$OD) δ ppm 2.34-2.45 (m, 4H), 2.48-2.56 (m, 4H), 2.64 (s, 3H), 2.86 (s, 3H), 3.90-3.98 (m, 2H), 5.38-5.44 (m, 1H), 7.99 (d, J=8.5 Hz, 2H), 8.12 (d, J=8.8 Hz, 2H); MS (DCI/NH$_3$) m/z=344 (M+H)$^+$. Anal. calcd. for C$_{18}$H$_{21}$N$_3$O$_2$S.1.20 CF$_3$CO$_2$H: C, 51.02; H, 4.66; N, 8.75. Found C, 51.23; H, 4.48; N, 8.70.

Example 34

N-[(endo)-8-Methyl-8-azabicyclo[3.2.1]octan-3-yl]-5-phenyl-1,3,4-thiadiazol-2-amine A solution of the product of Example 14A (0.17 g, 0.71 mmol) and (endo)-8-methyl-8-azabicyclo[3.2.1]octan-3-amine dihydrochloride (Apollo, 0.10 g, 0.7 mmol) in N,N-diisopropylethylamine (2 mL) and dimethyl sulfoxide (2 mL) was stirred in a sealed tube at 130° C. overnight. The mixture was cooled to room temperature and diluted with water (5 mL), extracted with CHCl$_3$ (4×10 mL). The combined extracts were washed with brine (2×5 mL) and concentrated under reduced pressure. The residue was purified by preparative HPLC (Gilson, Xterra® column, 7 µm, 40×100 mm, eluting solvent, MeCN/H$_2$O (with 0.1 M NH$_4$HCO$_3$/NH$_4$OH, PH=10) (v. 90/10 to 10/90 over 25 minutes), flow rate, 40 mL/min., uv, 254 nm) to provide the titled compound. $^1$H NMR (300 MHz, DMSO-D$_6$) δ ppm 1.71-1.98 (m, 6H), 1.99-2.11 (m, 2H), 2.16 (s, 3H), 2.96-3.08 (m, 2H), 3.81 (t, J=6.44 Hz, 1H), 7.30-7.57 (m, 3H), 7.67-7.95 (m, 2H); MS (DCI/NH$_3$) m/z 301 (M+1)$^+$.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

A pharmaceutically acceptable carrier means a non-toxic, inert solid, semi-solid or liquid filler, diluent, encapsulating material or formulation auxiliary of any type. Some examples of materials that can serve as pharmaceutically acceptable carriers are sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; cocoa butter and suppository waxes; oils, such as peanut oil, cottonseed oil, safflower oil, sesame oil, olive oil, corn oil and soybean oil; glycols, such a propylene glycol; esters, such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions. Other components, such as non-toxic compatible lubricants, such as sodium lauryl sulfate and magnesium stearate; coloring agents, releasing agents, coating agents, sweetening, flavoring and perfuming agents, preservatives and antioxidants can also be present in the composition.

The pharmaceutical compositions of the invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection include pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters, such as ethyl oleate, or suitable mixtures thereof. Suitable fluidity of the composition can be maintained, for example, by the use of a coating, such as lecithin; by the maintenance of the required particle size in the case of dispersions, and by the use of surfactants.

These compositions can also contain adjuvants, such as preservative agents, wetting agents, emulsifying agents, and dispersing agents. Prevention of the action of microorganisms can be ensured by various antibacterial and antifungal agents; for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, dissolving or suspending the drug in an oil vehicle can administer a parenterally administered drug form.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems, such as polymer matrices, liposomes, and microspheres. They can be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers, such as polylactide-polyglycolide. Depending upon the ratio of drug to polymer and the nature of the particular polymer used, the rate of drug release can be controlled. Examples of other biodegradable polymers include poly(orthoesters) and poly (anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions, can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be used are water, Ringer's solution, U.S.P. and isotonic sodium chloride solution. In addition, sterile, fixed oils are conventionally used as a solvent or suspending medium. For this purpose any bland fixed oil can be used including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier, such as sodium citrate or dicalcium phosphate and/or fillers or extenders, such as starches, lactose, sucrose, glucose, mannitol, and salicylic acid; binders, such as carboxymethylcellulose, alginates, gelatin, polyvinylpyrrolidinone, sucrose, and acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as cetyl alcohol and glycerol monostearate; absorbents, such as kaolin and bentonite clay; and lubricants, such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be used as fillers in soft and hard-filled gelatin capsules using lactose or milk sugar as well as high molecular weight polyethylene glycols.

The solid dosage forms of tablets, dragees, capsules, pills, and granules can be prepared with coatings and shells, such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of the invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms can contain inert diluents commonly used in the art such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide; oils, such as cottonseed, groundnut, corn, germ, olive, castor, and sesame oils); glycerol, tetrahydrofurfuryl alcohol, polyethylene glycols and fatty acid esters of sorbitan, and mixtures thereof.

Besides inert diluents, the oral compositions can also include adjuvants, such as wetting agents, emulsifying and suspending agents, sweetening, flavoring, and perfuming agents.

Dosage forms for topical or transdermal administration of a compound of the invention include ointments, pastes, creams, lotions, gels, powders, solutions, sprays, inhalants or patches. Ophthalmic formulation, eardrops, eye ointments, powders and solutions are also contemplated.

Ointments, pastes, creams and gels can contain, in addition to an active compound of the invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of the invention, lactose, talc, silicic acid, aluminum hydroxide, calcium silicates and polyamide powder, or mixtures of these substances. Sprays can additionally contain customary propellants, such as chlorofluorohydrocarbons.

Compounds of the invention can be administered as liposomes. Liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the invention, stabilizers, preservatives, and the like. The preferred lipids are the natural and synthetic phospholipids and phosphatidylcholines (lecithins) used separately or together. Methods to form liposomes are known in the art. See, for example, Prescott, Ed., *Methods in Cell Biology*, Volume XIV, Academic Press, New York, N.Y., (1976), p 33 et seq.

Determination of Biological Activity

To determine the effectiveness of representative compounds of the invention as α7 nAChRs, the compounds of the invention were evaluated according to the [$^3$H]-methyllycaconitine (MLA) binding assay the [$^3$H]-DPPB binding assay, and/or the [$^3$H]-cytisine binding assay, which were performed as described below.

[$^3$H]-Cytisine Binding

Compounds of the invention were analyzed for their ability to compete for α4β2 nAChRs by co-incubating a test compound with a known α4β2 nAChR ligand, cytosine. Binding conditions were modified from the procedures described in Pabreza L A, Dhawan, S, Kellar K J, [$^3$H]-Cytisine Binding to Nicotinic Cholinergic Receptors in Brain, *Mol. Pharm.* 39: 9-12, 1991. Membrane enriched fractions from rat brain minus cerebellum (ABS Inc., Wilmington, Del.) were slowly thawed at 4° C., washed and resuspended in 30 volumes of BSS-Tris buffer (120 mM NaCl/5 mM KCl/2 mM CaCl$_2$/2 mM MgCl$_2$/50 mM Tris-Cl, pH 7.4, 4° C.). Samples containing 100-200 μg of protein and 0.75 nM [$^3$H]-cytisine (30 C$_i$/mmol; Perkin Elmer/NEN Life Science Products, Boston, Mass.) were incubated in a final volume of 500 μL for 75 minutes at 4° C. Seven log-dilution concentrations of each compound were tested in duplicate. Non-specific binding was determined in the presence of 10 μM (–)-nicotine. Bound radioactivity was isolated by vacuum filtration onto prewetted glass fiber filter plates (Millipore, Bedford, Mass.) using a 96-well filtration apparatus (Packard Instruments, Meriden, Conn.) and were then rapidly rinsed with 2 mL of ice-cold BSS buffer (120 mM NaCl/5 mM KCl/2 mM CaCl$_2$/2 mM MgCl$_2$). PACKARD MICROSCINT-20® scintillation cocktail (40 μL) was added to each well and radioactivity determined using a PACKARD TOPCOUNT® instrument. The IC$_{50}$ values were determined by nonlinear regression in MICROSOFT EXCEL® software. K$_i$ values were calculated from the IC$_{50}$s using the Cheng-Prusoff equation, where $K_i = IC_{50}/(1+[Ligand]/K_D)$.

[$^3$H]-Methyllycaconitine (MLA) Binding

Compounds of the invention were analyzed for their ability to compete for α7 nAChRs by co-incubating a test compound with a known α7 nAChR ligand, MLA. Binding conditions were similar to those for [³H]-cytisine binding. Membrane enriched fractions from rat brain minus cerebellum (ABS Inc., Wilmington, Del.) were slowly thawed at 4° C., washed and resuspended in 30 volumes of BSS-Tris buffer (120 mM NaCl, 5 mM KCl, 2 mM $CaCl_2$, 2 mM $MgCl_2$, and 50 mM Tris-Cl, pH 7.4, 22° C.). Samples containing 100-200 µg of protein, 5 nM [³H]-MLA (25 $C_i$/mmol; Perkin Elmer/NEN Life Science Products, Boston, Mass.) and 0.1% bovine serum albumin (BSA, Millipore, Bedford, Mass.) were incubated in a final volume of 500 µL for 60 minutes at 22° C. Seven log-dilution concentrations of each compound were tested in duplicate. Non-specific binding was determined in the presence of 10 µM MLA. Bound radioactivity was isolated by vacuum filtration onto glass fiber filter plates prewetted with 2% BSA using a 96-well filtration apparatus (Packard Instruments, Meriden, Conn.) and were then rapidly rinsed with 2 mL of ice-cold BSS. Packard MICROSCINT-20® scintillation cocktail (40 µL) was added to each well and radioactivity was determined using a Packard TOPCOUNT® instrument. The $IC_{50}$ values were determined by nonlinear regression in Microsoft EXCEL® software. $K_i$ values were calculated from the $IC_{50}$s using the Cheng-Prusoff equation, where $K_i=IC_{50}/(1+[Ligand]/K_D)$.

[³H]-DPPB Binding

Compounds of the invention were analyzed for their ability to compete for α7 nAChRs by co-incubating a test compound with a known α7 nAChR ligand, DPPB, which is (S,S)-2,2-dimethyl-5-(6-phenyl-pyridazin-3-yl)-5-aza-2-azonia-bicyclo[2.2.1]heptane iodide. Procedures for preparing radiolabeled DPPB, [³H]-DPPB, are described below. Binding to the α7 nAChR subtype was determined using membrane enriched fractions from rat brain minus cerebellum or human cortex (ABS Inc., Wilmington, Del.). Pellets were thawed at 4° C., washed and resuspended with a Polytron at a setting of 7 in 30 volumes of BSS-Tris buffer (120 mM NaCl, 5 mM KCl, 2 mM $CaCl_2$, 2 mM $MgCl_2$, and 50 mM Tris-Cl, pH 7.4, 4° C.). Seven log-dilution concentrations of test compounds containing 100-200 µg of protein, and 0.5 nM [³H]-DPPB (62.8 Ci/mmol; R46V, Abbott Labs) were incubated in a final volume of 500 µl for 75 minutes at 4° C. in duplicate. Non-specific binding was determined in the presence of 10 µM methyllycaconitine. Bound radioactivity was collected on Millipore MULTISCREEN® harvest plates FB presoaked with 0.3% PEI using a Packard cell harvester, washed with 2.5 ml ice-cold buffer, and radioactivity determined using a Packard TOPCOUNT® Microplate beta counter. $IC_{50}$ values were determined by nonlinear regression in Microsoft® Excel or Assay Explorer. $K_i$ values were calculated from the $IC_{50}$s using the Cheng-Prusoff equation, where $K_i=IC_{50}/(1+[Ligand]/K_D)$. [³H]-DPPB was obtained according to the following preparation procedure.

Preparation of [Methyl-³H]2,2-Dimethyl-5-(6-phenyl-pyridazin-3-yl)-5-aza-2-azonia-bicyclo[2.2.1]heptane iodide

[Methyl-³H]2,2-dimethyl-5-(6-phenyl-pyridazin-3-yl)-5-aza-2-azonia-bicyclo[2.2.1]heptane iodide used in the [³H]-DPPB binding assay above was prepared according to the following procedures.

Step 1: Preparation of t-Butyl (S,S)-5-(6-Phenyl-pyridazin-3-yl)-2,5-diazabicyclo[2.2.1]heptane-2-carboxylate Triethylamine (20 mL) was added to a suspension of t-butyl (S,S)-2,5-diazabicyclo[2.2.1]heptane-2-carboxylate (3.43 g, 17.3 mmol, Aldrich Chemical Company) and 3-chloro-6-phenylpyridazine (3.30 g, 17.3 mmol, Aldrich Chemical Company) in toluene (50 mL), and the mixture was heated under nitrogen at 100° C. for 7 days. The dark mixture was cooled to room temperature, and the resulting precipitate was isolated by filtration, washed with toluene (15 mL) and dried under vacuum to provide the title compound as an off-white solid (3.00 g). The filtrate was concentrated, and the residue was purified by column chromatography on silica gel, eluting with ethyl acetate, to provide additional product (0.41 g, total yield 3.41 g, 56%): MS ($DCI/NH_3$) m/z 353 $(M+H)^+$.

Step 2: Preparation of (S,S)-2-Methyl 5-(6-phenyl-pyridazin-3-yl)-2,5-diazabicyclo[2.2.1]heptane The product obtained from Step 1 (3.41 g, 9.7 mmol) was dissolved in formic acid (20 mL) and treated with formalin (37% by weight, 1.0 g, 12.3 mmol). The mixture was heated at 100° C. for 1 hour, and the brown solution was cooled to room temperature and concentrated under vacuum. The residue was purified by column chromatography on silica gel, eluting with $CH_2Cl_2$—$CH_3OH$—$NH_4OH$ (95:5:1) to provide the title compound as an off-white solid (2.50 g, 96%): MS ($DCI/NH_3$) m/z 267 $(M+H)^+$.

Step 3: Preparation of [³H]-(S,S)-2,2-Dimethyl-5-(6-phenyl-pyridazin-3-yl)-5-aza-2-azonia-bicyclo[2.2.1]heptane iodide ([³H]-DPPB)

[³H]Methyl iodide in toluene (250 mCi in 0.1 mL, 85 Ci/mmol, American Radiolabeled Chemicals, Inc.) was combined with a solution of the product obtained from Step 2 in dichloromethane (0.788 mg, 2.96 µmole in 0.45 mL). The vial was capped and the mixture was allowed to react overnight at room temperature. Methanol was added, and the solvents were evaporated to give 42 mCi. The product was taken up in methanol for HPLC purification.

Step 4: Purification by High Performance Liquid Chromatography (HPLC)

About 7 mCi of [³H]-DPPB was evaporated to dryness, and the residue was dissolved in total about 4.5 ml acetonitrile:water:TFA (15:85:0.1). Approximately 0.9 mL per injection was made onto a PhenomenexLuna C18(2) column (5 µm, 250 mm×4.6 mm ID) using an Agilent HPLC system. [³H]-DPPB was eluted by a gradient mobile phase from 10% B to 20% B in 20 min where Mobile Phase A=0.1% trifluoroacetic acid in water and Mobile Phase B=0.1% trifluoroacetic acid in acetonitrile at a flow rate of approximately 1 mL/min. Peak detection and chromatograms were obtained with an Agilent variable wavelength UV detector set at 275 nm. The fractions containing [³H]-DPPB were collected at approximately 14 minutes using an Agilent fraction collector. The fractions were combined and the solvents were evaporated in vacuo. The residue was dissolved in 200 proof ethanol (2 mL) to give 0.7 mCi.

Step 5: Determination of Purity and Specific Activity

[³H]-DPPB was assayed using an Agilent 1100 series HPLC system consisting of a quaternary pump, an autosampler, and a photodiode array UV detector. A Packard Radiomatic A 500 radioactivity detector was connected to the HPLC system. For radiodetection, a 500 µL flow cell and a 3:1 ratio of Ultima-Flo M scintillation cocktail to HPLC mobile phase were used. The analyses were performed using a Phenomenex Luna C18(2) column (5 μm, 250 mm×4.6 mm ID). The mobile phase consisted of a gradient starting with 10% B and ramping to 20% B in 20 minutes followed by ramping to 90% B in 1 minute and hold at 90% B for 9 minutes, where Mobile Phase A=0.1% trifluoroacetic acid in water and Mobile Phase B=0.1% trifluoroacetic acid in acetonitrile. The flow rate was set at approximately 1 mL/min and the UV detection was set at 275 nm.

Compounds of the invention had $K_i$ values of from about 1 nanomolar to about 10 micromolar when tested by the [$^3$H]-MLA assay, many having a $K_i$ of less than 1 micromolar. [$^3$H]-cytisine binding values of compounds of the invention ranged from about 50 nanomolar to at least 100 micromolar. Preferred compounds typically exhibited greater potency at α7 receptors compared to α4β2 receptors. The determination of preferred compounds typically considered the $K_i$ value as measured by MLA assay in view of the $K_i$ value as measured by [$^3$H]-cytisine binding, such that in the formula D= $K_i^3{}_{H\text{-}cytisine}/K_{i\,MLA}$, D is greater than about 50. Alternatively, the $K_i$ value as measured by [$^3$H]-DPPB assay can be used in place of the $K_{i\,MLA}$ such that in the formula D'=$K_i^3{}_{H\text{-}cytisine}/K_{i[3H]\text{-}DPPB}$, D' is greater than about 50.

Compounds of the invention are α7 nAChRs ligands that modulate function of α7 nAChRs by altering the activity of the receptor or signaling. The compounds can be inverse agonists that inhibit the basal activity of the receptor or antagonists that completely block the action of receptor-activating agonists. The compounds also can be partial agonists that partially block or partially activate the α7 nAChR receptor or agonists that activate the receptor. Binding to α7 receptor also trigger key signaling processes involving various kinases and phosphatases and protein-protein interactions that are important to effects on memory, cytoprotection, gene transcription and disease modification.

Methods of the Invention

Compounds and compositions of the invention are useful for modulating the effects of nAChRs, and more particularly α7 nAChRs and α4β2 nAChRs. In particular, the compounds and compositions of the invention can be used for treating and preventing disorders modulated by α7 nAChRs. Typically, such disorders can be ameliorated by selectively modulating the α7 nAChRs in an animal, such as a human, preferably by administering a compound or composition of the invention, either alone or in combination with another active agent, for example, as part of a therapeutic regimen. Also, some compounds of the invention possess affinity at the α4β2 nAChRs in addition to α7 nAChRs, and selective compounds with dual affinities at both receptor subtypes have beneficial effects.

Conditions, Diseases and Disorders

Because α7-containing nAChRs have been shown to be involved in the neuroprotective effects of nicotine both in vitro and in vivo, the compounds of the invention can be used to treat neurodegeneration that underlies several progressive CNS disorders, such as Alzheimer's disease, Parkinson's disease, amyotrophic lateral sclerosis, Huntington's disease, dementia with Lewy bodies, as well as diminished CNS function resulting from traumatic brain injury. Compounds that activate α7 nAChRs can be used to counter the deficits of Alzheimer's and other neurodegenerative diseases.

Thus, α7 ligands can be used in the treatment schizophrenia. Activators of α7 receptors are useful for enhancing cognitive function in schizophrenic patients who are being treated with atypical antipsychotics. Accordingly, the combination of a α7 nAChR ligand and an atypical antipsychotic offer improved therapeutic utility. Specific examples of suitable atypical antipsychotics include, but are not limited to, clozapine, risperidone, olanzapine, quietapine, ziprasidone, zotepine, iloperidone, and the like.

Because improved angiogenesis has been shown to involve activation of the α7 nAChR, nAChR ligands that are selective for the α7 subtype can be used for stimulating angiogenesis with an improved side effect profile.

α7 nAChR ligands can be used to treat pain, including acute pain, post-surgical pain, as well as chronic pain states including inflammatory pain and neuropathic pain. They can also be used for treating conditions involving TNF-mediated diseases; for example, rheumatoid arthritis, Crohn's disease, ulcerative colitis, inflammatory bowel disease, organ transplant rejection, acute immune disease associated with organ transplantation, chronic immune disease associated with organ transplantation, septic shock, toxic shock syndrome, sepsis syndrome, depression, and rheumatoid spondylitis.

Because activation of an α7 nAChR on the sperm cell has been shown to be essential for the acrosome reaction, selective α7 agents of the invention can be used to treat fertility disorders.

Compounds of the invention are α7 nAChRs ligands that modulate function of α7 nAChRs by altering the activity of the receptor or signaling. The compounds can be inverse agonists that inhibit the basal activity of the receptor or antagonists that completely block the action of receptor-activating agonists. The compounds also can be partial agonists that partially block or partially activate the α7 nAChR receptor or agonists that activate the receptor. Binding to an α7 receptor also triggers key signaling processes involving various kinases and phosphatases and protein-protein interactions that are important to effects on memory, cytoprotection, gene transcription and disease modification. Therefore, the administration of a therapeutically effective amount of a compound of formula (I) to a mammal provides a method of selectively modulating the effects of α4β2, α7, or both α4β2 and α7 nicotinic acetylcholine receptors.

Nicotinic receptor modulation of dopine transmission has been identified as an important mechanism underlying various forms of substance abuse, including for example, smoking cessation, alcohol addition, cannibis addiction, and other forms of substances abuse. (Rose, J. E., Biochem Pharmacol., 74(8): 1263-1270, 2007; Rollema H., Coe J. W., Chambers L. K., Hurst R. S., Stahl S. M., Williams K. E., Trends Pharmacol Sci., 28(7): 316-25, 2007; Steensland P., Simms J. A., Holgate J., Richards J. K., Bartlett S. E., Proc Nat'l Acad Sci U.S.A., 104(30):12518-23, 2007; and Scherma m., Fattor Le., Stoik J., Wertheim C., Tanda G., Fratta W., Goldberg S. R., 27(21): 5615-20, 2007). For example, nicotinic receptors including α4β2 and α7 nAChRs are present in brain pathways implicated in addiction. Accordingly, a method of selectively modulating the effects of α4β2, α7, or both α4β2 and α7 nicotinic acetylcholine receptors would be useful in treating or preventing substance abuse.

Therefore, the administration of a therapeutically effective amount of a compound of formula (I) to a mammal provides a method of treating or preventing a condition or disorder selected from the group consisting of attention deficit disorder, attention deficit hyperactivity disorder (ADHD), Alzheimer's disease (AD), mild cognitive impairment, senile dementia, AIDS dementia, Pick's Disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammatory pain, neuropathic pain, infertility, need for new blood vessel growth associated with wound healing, need for new blood vessel growth associated with vascularization of skin grafts, and lack of circulation, more particularly circulation around a vascular occlusion, rheumatoid arthritis, Crohn's disease, ulcerative colitis, inflammatory bowel disease, organ transplant rejection, acute immune disease associated with organ transplantation, chronic immune disease associated with organ transplantation, septic shock, toxic shock syndrome, sepsis syndrome, depression, rheumatoid spondylitis, and substance abuse. More preferred, the administration of a therapeutically effective amount of a compound of formula (I) to a mammal provides a method of treating cognitive disorders, neurodegeneration, and schizophrenia.

The compounds of the invention can be administered with other medications, either simultaneously, in combined formulations, or in a regimen where the compounds are administered separately. In addition to the atypical psychotics listed previously, the compounds of the invention can be administered compounds administered (or proposed to be administered) for the treatment of attention deficit hyperactivity disorder, such as dextroamphetamine, levoamphetamine, dextrothreomethylphenidate, levothreomethylphenidate, amantadine, aminedyne, benzphetamine, bupropion, clonidine, modafinil, pemoline, selegiline, magnesium, zinc, gingko biloba, fatty acids, B-vitamins, and milnacipran; with compounds administered in the treatment of Alzheimer's disease, such as acetylcholinesterase inhibitors (e.g., tacrine, donepezil, galanthamine and rivastigmine); memantine and other NMDA antagonists, vitamins C, and vitamin E.

Administration—Dosage

Actual dosage levels of active ingredients in the pharmaceutical compositions of the invention can be varied so as to obtain an amount of the active compound(s) that is effective to achieve the desired therapeutic response for a particular patient, compositions and mode of administration. The selected dosage level depends upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be used in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention decided by a treating physician within the scope of sound medical judgment.

The total daily dose of the compounds of the invention administered to a human or lower animal range from about 0.010 mg/kg body weight to about 1 g/kg body weight. More preferable doses can be in the range of from about 0.010 mg/kg body weight to about 100 mg/kg body weight. If desired, the effective daily dose can be divided into multiple doses for purposes of administration. Consequently, single dose compositions can contain such amounts or submultiples thereof to make up the daily dose.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, can be made without departing from the spirit and scope thereof.

We claim:

1. A compound of formula (I),

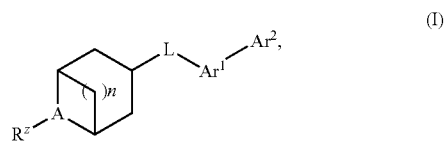

or a pharmaceutically acceptable salt thereof, wherein n is 1, 2 or 3;

A is N or $N^+$—$O^-$;

$R^z$ is hydrogen, alkyl, cycloalkyl or arylalkyl;

L is selected from the group consisting of O, S, and —$N(R_a)$—;

$Ar^1$ is a 5-membered heteroaryl group;

$Ar^2$ is an aryl or heteroaryl group; and $R_a$ is selected from the group consisting of hydrogen, alkyl and alkylcarbonyl.

2. The compound of claim 1, wherein $Ar^1$ is selected from the group consisting of:

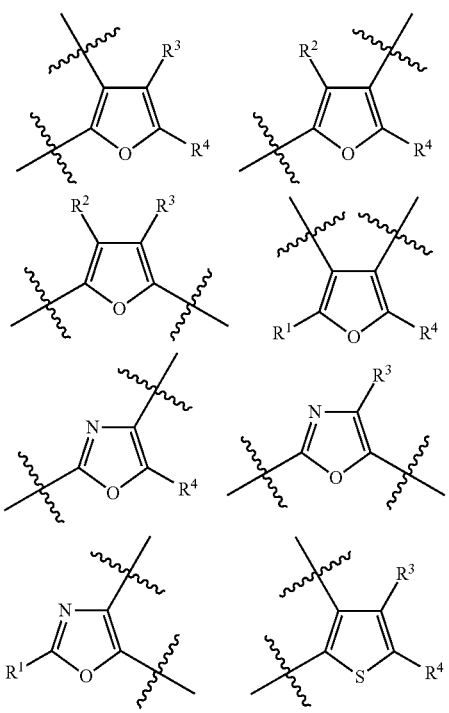

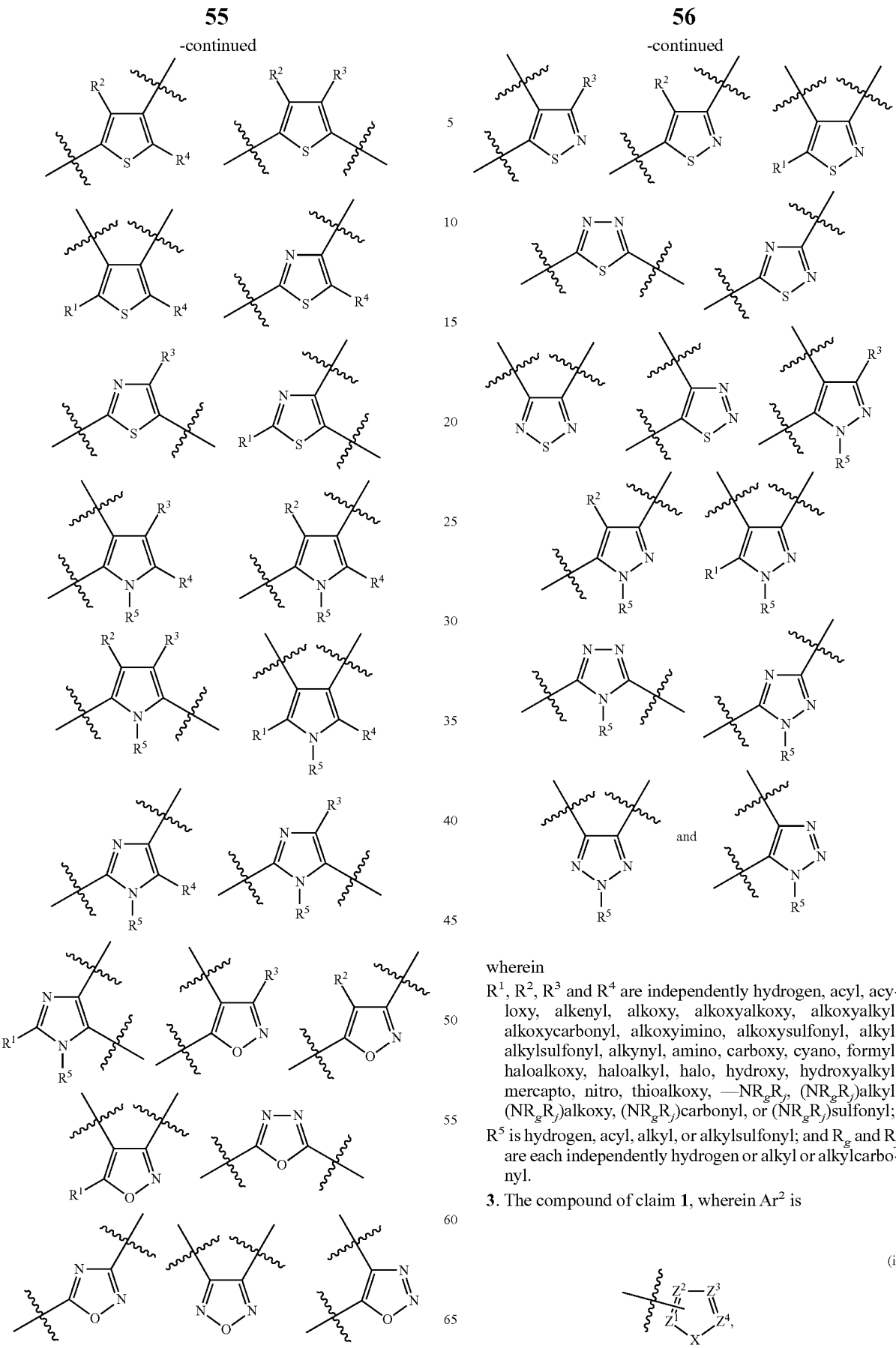

wherein
R[1], R[2], R[3] and R[4] are independently hydrogen, acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amino, carboxy, cyano, formyl, haloalkoxy, haloalkyl, halo, hydroxy, hydroxyalkyl, mercapto, nitro, thioalkoxy, —NR$_g$R$_j$, (NR$_g$R$_j$)alkyl, (NR$_g$R$_j$)alkoxy, (NR$_g$R$_j$)carbonyl, or (NR$_g$R$_j$)sulfonyl;
R[5] is hydrogen, acyl, alkyl, or alkylsulfonyl; and R$_g$ and R$_j$ are each independently hydrogen or alkyl or alkylcarbonyl.

3. The compound of claim 1, wherein Ar[2] is (i)

$$\begin{array}{c} Z^2\text{—}Z^3 \\ | \quad \| \\ Z^1 \quad Z^4 \\ \diagdown X \diagup \end{array}$$

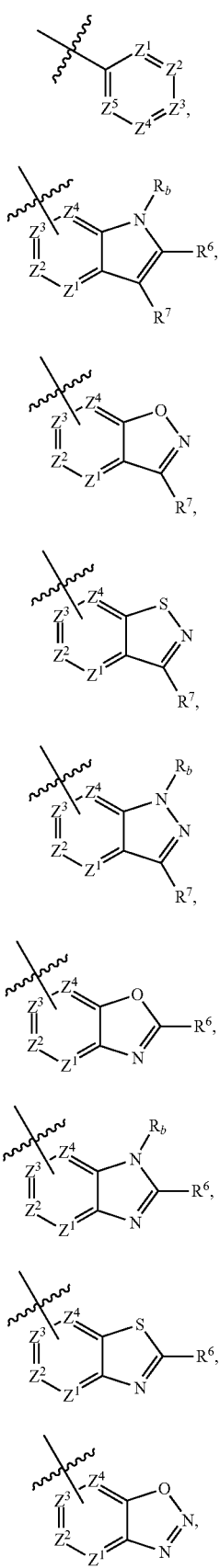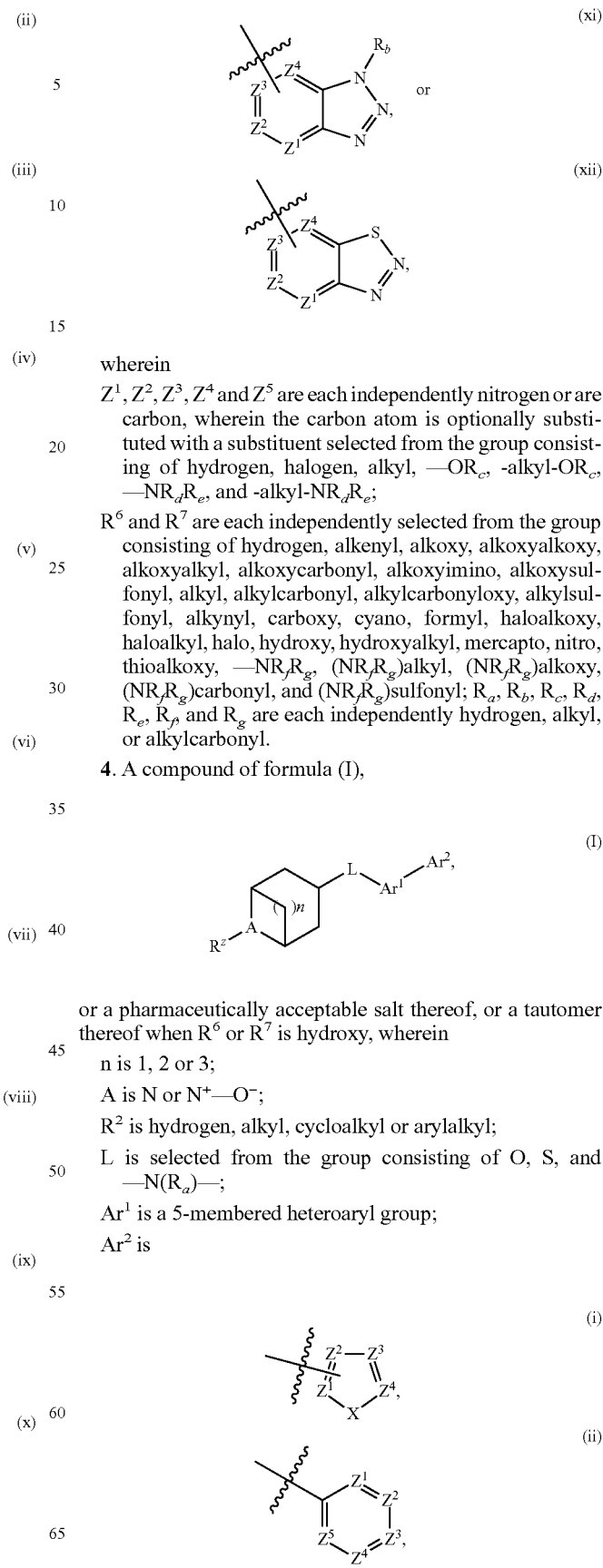

wherein
Z$^1$, Z$^2$, Z$^3$, Z$^4$ and Z$^5$ are each independently nitrogen or are carbon, wherein the carbon atom is optionally substituted with a substituent selected from the group consisting of hydrogen, halogen, alkyl, —OR$_c$, -alkyl-OR$_c$, —NR$_d$R$_e$, and -alkyl-NR$_d$R$_e$;
R$^6$ and R$^7$ are each independently selected from the group consisting of hydrogen, alkenyl, alkoxy, alkoxyalkoxy, alkoxyalkyl, alkoxycarbonyl, alkoxyimino, alkoxysulfonyl, alkyl, alkylcarbonyl, alkylcarbonyloxy, alkylsulfonyl, alkynyl, carboxy, cyano, formyl, haloalkoxy, haloalkyl, halo, hydroxy, hydroxyalkyl, mercapto, nitro, thioalkoxy, —NR$_f$R$_g$, (NR$_f$R$_g$)alkyl, (NR$_f$R$_g$)alkoxy, (NR$_f$R$_g$)carbonyl, and (NR$_f$R$_g$)sulfonyl; R$_a$, R$_b$, R$_c$, R$_d$, R$_e$, R$_f$, and R$_g$ are each independently hydrogen, alkyl, or alkylcarbonyl.

4. A compound of formula (I), $$\text{(I)}$$

or a pharmaceutically acceptable salt thereof, or a tautomer thereof when R$^6$ or R$^7$ is hydroxy, wherein
n is 1, 2 or 3;
A is N or N$^+$—O$^-$;
R$^2$ is hydrogen, alkyl, cycloalkyl or arylalkyl;
L is selected from the group consisting of O, S, and —N(R$_a$)—;
Ar$^1$ is a 5-membered heteroaryl group;
Ar$^2$ is -continued (iii) 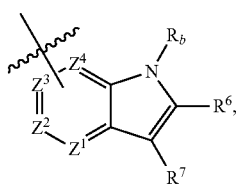

(iv) 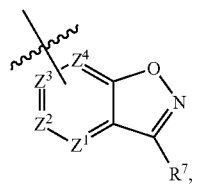

(v) 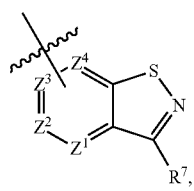

(vi) 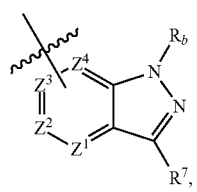

(vii) 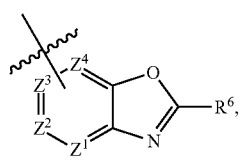

(viii) 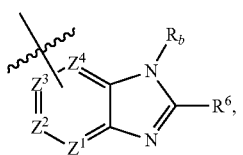

(ix) 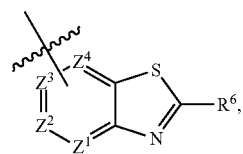

(x) 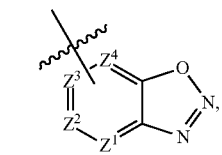

(xi) 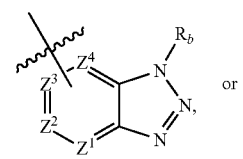 or

-continued (xii) 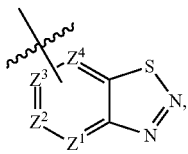

wherein $Z^1$, $Z^2$, $Z^3$, $Z^4$ and $Z^5$ are each independently nitrogen or are carbon, wherein the carbon atom is optionally substituted with a substituent selected from the group consisting of hydrogen, halogen, alkyl, —$OR_c$, -alkyl-$OR_c$, —$NR_dR_e$, and -alkyl-$NR_dR_e$;

$R^6$ and $R^7$ are each independently selected from the group consisting of hydrogen, alkenyl, alkoxy, alkoxyalkoxy, alkoxyalkyl, alkoxycarbonyl, alkoxyimino, alkoxysulfonyl, alkyl, alkylcarbonyl, alkylcarbonyloxy, alkylsulfonyl, alkynyl, carboxy, cyano, formyl, haloalkoxy, haloalkyl, halo, hydroxy, hydroxyalkyl, mercapto, nitro, thioalkoxy, —$NR_fR_g$, ($NR_fR_g$)alkyl, ($NR_fR_g$)alkoxy, ($NR_fR_g$)carbonyl, and ($NR_fR_g$)sulfonyl; $R_a$, $R_b$, $R_c$, $R_d$, $R_e$, $R_f$, and $R_g$ are each independently hydrogen, alkyl, or alkylcarbonyl.

5. The compound of claim 2, wherein

A is N;

$R^z$ is H or methyl;

L is O;

n is 2; and $Ar^1$ is:

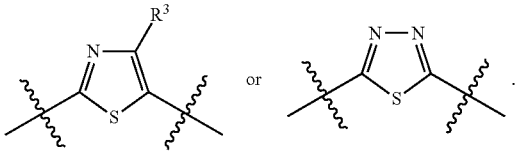

6. The compound of claim 3, wherein

A is N;

$R^z$ is H or methyl;

L is O;

n is 2;

$Ar^2$ is (iii) 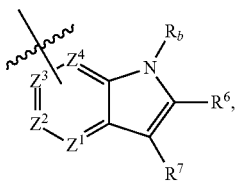

(vi) 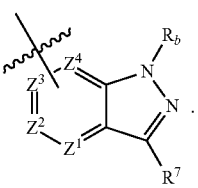

7. The compound of claim 2, wherein
A is N;
R² is H or methyl;
L is O;
n is 2;
Ar¹ is

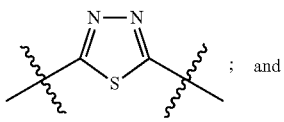 [SMILES: *c1nnc(*)s1]
; and

Ar² is

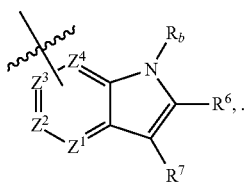
(iii)

8. The compound of claim 1, selected from the group consisting of:
2-[(endo)-8-Methyl-8-azabicyclo[3.2.1]octan-3-yloxy]-5-(1H-indol-5-yl)-thiazole;
2-[(endo)-8-Methyl-8-azabicyclo[3.2.1]octan-3-yloxy]-5-phenyl-thiazole;
2-[(endo)-8-Methyl-8-azabicyclo[3.2.1]octan-3-yloxy]-5-(pyridin-3-yl)-thiazole;
5-(1H-Indol-6-yl)-2-[(endo)-8-methyl-8-azabicyclo[3.2.1]octan-3-yloxy]thiazole;
5-(1H-Indol-4-yl)-2-[(endo)-8-methyl-8-azabicyclo[3.2.1]octan-3-yloxy]thiazole;
5-(Benzofuran-5-yl)-2-[(endo)-8-methyl-8-azabicyclo[3.2.1]octan-3-yloxy]thiazole;
5-(Benzo[b]thiophen-5-yl)-2-[(endo)-8-methyl-8-azabicyclo[3.2.1]octan-3-yloxy]thiazole;
5-(2-(Trifluoromethyl)-1H-indol-5-yl)-2-[(endo)-8-methyl-8-azabicyclo[3.2.1]octan-3-yloxy]thiazole;
5-(Dibenzo[b,d]thiophen-2-yl)-2-[(endo)-8-methyl-8-azabicyclo[3.2.1]octan-3-yloxy]thiazole;
2-[(exo)-8-Methyl-8-azabicyclo[3.2.1]octan-3-yloxy]-5-(1H-indol-5-yl)-thiazole;
2-[(exo)-8-Methyl-8-azabicyclo[3.2.1]octan-3-yloxy]-5-(1H-indol-6-yl)-thiazole;
2-[(exo)-8-Methyl-8-azabicyclo[3.2.1]octan-3-yloxy]-5-phenyl-thiazole;
2-[(exo)-8-Methyl-8-azabicyclo[3.2.1]octan-3-yloxy]-5-(pyridin-3-yl)-thiazole;
2-[(endo)-8-methyl-8-azabicyclo[3.2.1]octan-3-yloxy]-5-phenyl-1,3,4-thiadiazole;
2-(1H-Indol-5-yl)-5-[(endo)-8-methyl-8-azabicyclo[3.2.1]octan-3-yloxy]-1,3,4-thiadiazole;
2-(Benzofuran-5-yl)-5-[(endo)-8-methyl-8-azabicyclo[3.2.1]octan-3-yloxy]-1,3,4-thiadiazole;
2-(Benzo[b]thiophen-5-yl)-5-[(endo)-8-methyl-8-azabicyclo[3.2.1]octan-3-yloxy]-1,3,4-thiadiazole;
2-(3-Fluorophenyl)-5-[(endo)-8-methyl-8-azabicyclo[3.2.1]octan-3-yloxy]-1,3,4-thiadiazole;
2-[(endo)-8-Methyl-8-azabicyclo[3.2.1]octan-3-yloxy]-5-m-tolyl-1,3,4-thiadiazole;
2-(4-Fluorophenyl)-5-[(endo)-8-methyl-8-azabicyclo[3.2.1]octan-3-yloxy]-1,3,4-thiadiazole;
2-(3-Chlorophenyl)-5-[(endo)-8-methyl-8-azabicyclo[3.2.1]octan-3-yloxy]-1,3,4-thiadiazole;
2-(1H-Indol-6-yl)-5-[(endo)-8-methyl-8-azabicyclo[3.2.1]octan-3-yloxy]-1,3,4-thiadiazole;
2-(1H-Indol-4-yl)-5-[(endo)-8-methyl-8-azabicyclo[3.2.1]octan-3-yloxy]-1,3,4-thiadiazole;
2-(3-Cyanophenyl)-5-[(endo)-8-methyl-8-azabicyclo[3.2.1]octan-3-yloxy]-1,3,4-thiadiazole;
2-(3-Trifluoromethylphenyl)-5-[(endo)-8-methyl-8-azabicyclo[3.2.1]octan-3-yloxy)-1,3,4-thiadiazole;
2-(4-Chlorophenyl)-5-((1R,3R,5S)-8-methyl-8-azabicyclo[3.2.1]octan-3-yloxy)-1,3,4-thiadiazole;
2-(2-(Trifluoromethyl)-1H-indol-5-yl)-5-[(endo)-8-methyl-8-azabicyclo[3.2.1]octan-3-yloxy]-1,3,4-thiadiazole;
2-(3-Chloro-4-fluorophenyl)-5-[(endo)-8-methyl-8-azabicyclo[3.2.1]octan-3-yloxy)-1,3,4-thiadiazole;
2-(4-(Trifluoromethyl)phenyl)-5-[(endo)-8-methyl-8-azabicyclo[3.2.1]octan-3-yloxy]-1,3,4-thiadiazole;
2-(4-Methoxyphenyl)-5-[(endo)-8-methyl-8-azabicyclo[3.2.1]octan-3-yloxy]-1,3,4-thiadiazole;
2-(3-Aminophenyl)-5-[(endo)-8-methyl-8-azabicyclo[3.2.1]octan-3-yloxy]-1,3,4-thiadiazole;
2-(4-Ethylphenyl)-5-[(endo)-8-methyl-8-azabicyclo[3.2.1]octan-3-yloxy]-1,3,4-thiadiazole;
2-(4-Acetylphenyl)-5-[(endo)-8-methyl-8-azabicyclo[3.2.1]octan-3-yloxy]-1,3,4-thiadiazole; and
N-[(endo)-8-Methyl-8-azabicyclo[3.2.1]octan-3-yl]-5-phenyl-1,3,4-thiadiazol-2-amine.

9. A pharmaceutical composition comprising a therapeutically effective amount of a compound of claim 1 and a pharmaceutically acceptable carrier.

10. A method of selectively modulating the effects of α7 nicotinic acetylcholine receptors, α4β2 nicotinic acetylcholine receptors, or both α7 and α4β2 nicotinic acetylcholine receptors in a mammal comprising administering an effective amount of a compound of claim 1 to said mammal.

11. The method of claim 10, wherein said compound is an agonist of at least one α7 and α4β2 nicotinic acetylcholine receptor.

12. A method of treating a α7 and α4β2 nicotinic acetylcholine receptor-mediated condition or disorder of a subject, the method comprising administering a compound of claim 1 to the subject in need thereof, wherein the α7 and α4β2 nicotinic acetylcholine receptor-mediated condition or disorder is selected from the group consisting of a cognitive disorder, attention deficit disorder, attention deficit hyperactivity disorder, Alzheimer's disease, mild cognitive impairment, senile dementia, AIDS dementia, Pick's Disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammation, inflammatory pain, neuropathic pain, infertility, need for new blood vessel growth associated with wound healing, need for new blood vessel growth associated with vascularization of skin grafts, and lack of circulation, rheumatoid arthritis, Crohn's disease, ulcerative colitis, inflammatory bowel disease, organ transplant rejection, acute immune disease associated with organ transplantation, chronic immune disease associated with organ transplantation, septic shock, toxic shock syndrome, sepsis syndrome, depression, rheumatoid spondylitis, and substance abuse.

13. The method according to claim 12, wherein said compound is an agonist of at least one α7 nicotinic acetylcholine receptor, and wherein the method further comprises administering an atypical antipsychotic.

14. The method of claim 13, wherein the atypical antipsychotic is at least one selected from the group consisting of clozapine, risperidone, olanzapine, quietapine, ziprasidone, zotepine, and ioperidone.

15. The method of claim 10, further comprising administering said compound with a second composition used to treat cognitive disorders.

16. The method of claim 15, wherein the cognitive disorder is attention deficit disorder, and the second composition comprises at least one selected from the group consisting of dextroamphetamine, levoamphetamine, dextrothreomethylphenidate, levothreomethylphenidate, amantadine, amineptine, benzphetamine, bupropion, clonidine, modafinil, pemoline, selegiline, and milnacipran.

17. The method of claim 15, wherein the cognitive disorder is Alzheimer's disease, and the second composition comprises at least one selected from the group consisting of an acetylcholinesterase inhibitor, a NMDA antagonist, vitamin C, and vitamin E.

* * * * *